US010059673B2

(12) United States Patent
Pazenok

(10) Patent No.: US 10,059,673 B2
(45) Date of Patent: Aug. 28, 2018

(54) PROCESS FOR THE PREPARATION OF 5-FLUORO-1H-PYRAZOLES STARTING FROM HEXAFLUOROPROPENE

(71) Applicant: BAYER CROPSCIENCE AKTIENGESELLSCHAFT, Monheim am Rhein (DE)

(72) Inventor: Sergii Pazenok, Solingen (DE)

(73) Assignee: BAYER CROPSCIENCE AKTIENGESELLSCHAFT, Monheim am Rhein (DE)

( * ) Notice: Subject to any disclaimer, the term of this patent is extended or adjusted under 35 U.S.C. 154(b) by 0 days.

(21) Appl. No.: 15/504,294

(22) PCT Filed: Aug. 14, 2015

(86) PCT No.: PCT/EP2015/068782
§ 371 (c)(1),
(2) Date: Feb. 15, 2017

(87) PCT Pub. No.: WO2016/026789
PCT Pub. Date: Feb. 25, 2016

(65) Prior Publication Data
US 2017/0233348 A1   Aug. 17, 2017

(30) Foreign Application Priority Data
Aug. 19, 2014   (EP) .................................. 14181402

(51) Int. Cl.
*C07D 231/16*   (2006.01)
*C07D 231/38*   (2006.01)
*C07D 403/04*   (2006.01)
*C07C 17/358*   (2006.01)
*C07C 17/26*    (2006.01)

(52) U.S. Cl.
CPC ............ *C07D 231/16* (2013.01); *C07C 17/26* (2013.01); *C07C 17/358* (2013.01); *C07D 231/38* (2013.01); *C07D 403/04* (2013.01)

(58) Field of Classification Search
None
See application file for complete search history.

(56) References Cited
U.S. PATENT DOCUMENTS

| | | | |
|---|---|---|---|
| 2,918,501 | A | 2/1958 | Warren et al. |
| 4,093,670 | A | 6/1978 | Ozawa et al. |
| 4,377,717 | A | 3/1983 | Anello et al. |
| 5,254,774 | A | 10/1993 | Prokop |
| 8,946,234 | B2 | 2/2015 | Maue et al. |
| 2015/0099766 | A1 | 4/2015 | Maue et al. |

FOREIGN PATENT DOCUMENTS

| | | |
|---|---|---|
| CN | 103483139 A | 1/2014 |
| DE | 2706603 A1 | 9/1977 |
| DE | 4228592 A1 | 3/1994 |
| EP | 2184273 A1 | 5/2010 |
| WO | 2005040110 A1 | 5/2005 |
| WO | 2009089508 A1 | 7/2009 |
| WO | 2010/051926 A2 | 5/2010 |
| WO | 2010/123999 A2 | 10/2010 |
| WO | 2011012620 A2 | 2/2011 |
| WO | 2012/069366 A1 | 5/2012 |
| WO | 2012/107343 A1 | 8/2012 |

OTHER PUBLICATIONS

International Search Report of PCT/EP2015/068782 dated Oct. 5, 2015.
Remzi et al., "Click Chemistry beyond Metal-Catalyzed Cycloaddition" Angew. Chem. Int. Ed. (2009). vol. 48: 4900-4908.
Bock et al., "CuI-Catalyzed Alkyne-Azide "Click" Cycloadditons from a Mechanistic and Synthetic Perspective" Eur. J. Org. Chem. (2006). pp. 51-68.
Chambers et al., "Reactions involving fluoride ion. Part 37*. 'Proton Sponge' hydrofluoride as fluoride ion donor" Journal of Fluorine Chemistry. (1994) vol. 69: 103-108.
Koenig et al., "Eine neue Methode zur Synthese vonn Peptiden: Aktivierung der Carboxylgruppe mit Dicyclohexylcarbodiimid unter Zusatz von 1-Hydroxy-benzotriazolen" Chem. Ber. (1970) vol. 103: 788-798.
Furin et al., "Reactions of Perfluoro(5-aza-4-nonene) with Hydrazine and Some Its Derivatives" Russian Journal of Organic Chemistry. (2001) vol. 37, No. 11: 1621-1628.
Guida et al., "Phase-Transfer Alkylation of Heterocycles in the Presence of 18-Crown-6 and Potassium tert-Butoxide" J. Org. Chem. (1980) vol. 45: 3172-3176.
Haase et al., Chemische Berichte, (1904), vol. 37:3228-3238.
Chi et al., "Synthesis of fluorinated N-arylpyrazoles with perfluoro-2-mthyl-2-pentene and arylhydrazines" Journal of Fluorine Chemistry. (1999) vol. 98: 29-36.
Anderson et al., "A Reinvestigation of the Mixed Carbonic Anhydride Method of Peptide Synthesis" Journal of American Chemical Society. (Sep. 13, 1967) 89:19: 5012-5017.
Brunskill et al., "Anionic Oligomerisation of Hexafluoropropene : Fission of a Carbon-Carbon Bond by Fluoride Ion" Chemical Communications. (1970) pp. 1444-1446.
Chambers et al., "Reactions involving fluoride ion. Part 401. Amines as Initiators of Fluoride Ion Catalysed Reactions" Tetrahedron. (1995) vol. 51, No. 48: 13167-13176.
Lutz et al., "Copper-Free Azide-Alkyne Cycloadditions: New Insights and Perspectives" Angew. Chem. Int. Ed. (2008) vol. 47: 2182-2184.
Martini et al., "Uber die Umsetzung von Hexabluorpropen and Perfluor-2-methyl-2-penten mit Wasser" Journal of Fluorine Chemistry. (1976) vol. 8: 535-540.
Pasenok et al., "Utilisation of Ammonium and Phosphonium Perfluorocyclobutane Ylides as Fluoride Anion Source" Tetrahedron. (1996) vol. 52, No. 29: 9755-9758.

(Continued)

*Primary Examiner* — Kamal A Saeed
(74) *Attorney, Agent, or Firm* — McBee Moore Woodward & Vanik IP, LLC

(57) ABSTRACT

A new process for the preparation of 5-fluoro-1H-pyrazoles of the general formula (I) as described herein and further reactions with this compound.

14 Claims, No Drawings

(56) References Cited

OTHER PUBLICATIONS

Perlow et al., "Use of N-Fmoc Amino Acid Chlorides and Activated 2-(Fluorenylmethoxy)-5(4H)-oxazolones in Solid-Phase Peptide Synthsis" J. Org. Chem. (1992) vol. 57: 4394-4400.
Scherer et al., Journal of Organic Chemistry. (1981) vol. 46: 2379-2381.
Snegirev et al., Seriya Khimicheskaya (1986), vol. 1: 106-119.
Spivey et al., "Solid-Phase Synthesis of an A-B Loop Mimetic of the C3 Domain of Human IgE: Macrocyclization by Sonogashira Coupling" Journal of Organic Chemistry. (2003) vol. 68: 1843-1851.
Williams et al., "Development of a Novel Class of Cyclic Hexapeptide Oxytocin Antagonists Based on a Natural Product" J. Med. Chem. (1992) vol. 35: 3905-3915.

PROCESS FOR THE PREPARATION OF 5-FLUORO-1H-PYRAZOLES STARTING FROM HEXAFLUOROPROPENE

CROSS-REFERENCE TO RELATED APPLICATIONS

This application is a National Stage entry of International Application No. PCT/EP2015/068782 filed 14 Aug. 2015, which claims priority to European Patent Applications No. 14181402.0, filed 19 Aug. 2014.

BACKGROUND OF THE INVENTION

Field of the Invention 5-fluoro-1H-pyrazoles, in particular 5-Fluoro-1-methyl-3-pentafluoroethyl-4-trifluoromethyl-1H-pyrazole, are important building blocks for the preparation of crop protection chemicals, as those described in WO 2010051926, WO 2012/069366, WO 2012/0803876 and WO 2012/107343.

Description of Related Art

For the dimerization of hexafluoropropene (HFP) to perfluoro-4-methyl-2-pentene different catalyst and processes have been used.

Perfluoro-2-methyl-2-pentene is commercially available (Fa. Daikin) and P&M Invest (Russia). However, the compound is toxic.

Alternatively, it can be prepared via dimerization of hexafluoropropene (see, e.g., U.S. Pat. No. 5,254,774; R. Haszeldiner et al, Journal of the Chemical Society D: Chemical Communications (1970), (21), 1444-1445.

DE 4228592 describes the preparation of perfluoro-4-methyl-2-pentene in the presence of N,N,N,N-Tetramethylethylendiamin and Kaliumfluoride.

Pazenok et al. describes the preparation of perfluoro-4-methyl-2-pentene in the presence of ammonium and phosphonium perfluorocyclobutane ylides (Pazenok et al., Tetrahedron Letters, (1996), 52(29), 9755-9758).

U.S. Pat. No. 5,254,774 describes the preparation of hexafluoropropene oligomers in the presence of potassium cyanide.

U.S. Pat. No. 2,918,501 describes the preparation of internally unsaturated perfluoroolefins in the presence of fluoride in different solvents like amides, phenylamine or sulfoxides.

For the transformation of perfluoro-4-methyl-2-pentene into perfluoro-2-methyl-2-pentene usually fluorides are used (Brunskill et al, Chem. Com. 1970, 1444).

Also 'Proton Sponge' hydrofluoride has been used to generate carbanions from hexafluoropropene (Chambers et al, J. of Fluorine Chemistry (1994), 69(1), 103-108).

U.S. Pat. No. 4,377,717 discloses the production of perfluoro-2-methyl-2-pentene by heating hexafluoropropylene in the presence of activated carbon.

U.S. Pat. No. 4,093,670 (DE 2706603 A1) discloses the production of perfluoro-4-methyl-2-pentene. $(E)(CF_3)_2CFCF=CF(CF_3)$ was isomerized to the more stable perfluoro-2-methyl-2-pentene upon heating for 3 h at 40° in MeCN in the presence of 0.00025 mol each of KF and 18-crown-6 ether. In other examples the 18-crown-6 ether was replaced by benzo-15-crown-5 ether and dibenzo- and dicyclohexyl-18-crown-6 ether.

CN 103483139 discloses a perfluoro-2-methyl-2-pentene preparation method. The method allows perfluoro-2-methyl-2-pentene to be prepared through a catalytic isomerization reaction of a raw material perfluoro-4-methyl-2-pentene.

A method of preparing of perfluoro-2-methyl-2-penten-)3-enolate is described in: V. Snegirev et al Izvestiya Akademii Nauk SSR, Seriya Khimicheskaya (1986), N. 1, pp. 106-119; and T. Martini, J. Fluor. Chem. (1976), 8, 535-540. Scherer 46 et al (1981) J. of Organic Chemistry 2379-2381 and Chambers et al 51 (1995) Tetrahedron 48, 13167-13176 disclose dimerization processes of $CF_2=CF(CF_3)$.

It is known that 5-fluoro-1-methyl-3-pentafluoroethyl-4-trifluoromethyl-1H-pyrazole can be prepared by the treatment of the dimer of hexafluoropropene with water free N,N-dimethylhydrazine in diethyl ether at −50° C. followed by heating of the intermediate at 120° C., Knunyants et al. Izv. Akad. Nauk SSSR (1990) 2583-2589:

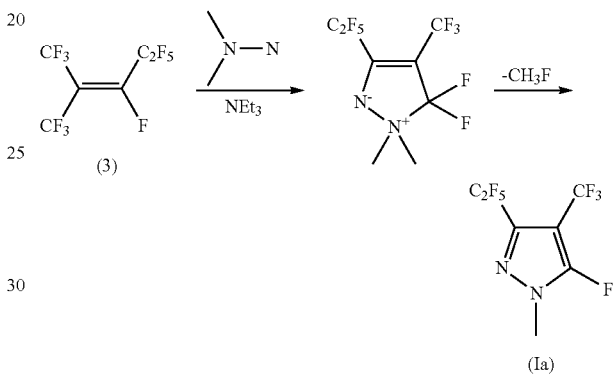

However, this two steps transformation requires low temperatures for the first step and results in the formation of $CH_3F$ during the thermal elimination in the second step, making this process expensive, environmentally unfriendly, and particularly difficult for industrialization.

Starting from perfluoro-2-methyl-2-penten and phenylhydrazine, in the presence of triethylamine at −50° C. 1-Phenylpyrazole has been shown to be obtainable in 90% yield (SU 1456419).

Chi et al. J. Fluor. Chem. 98 (1999) 29, reported that the reaction of perfluoro-2-methyl-2-pentene (3) with phenylhydrazine in $CH_3CN$ gave a mixture of isomeric pyrazoles a and b in a ratio 4:1.

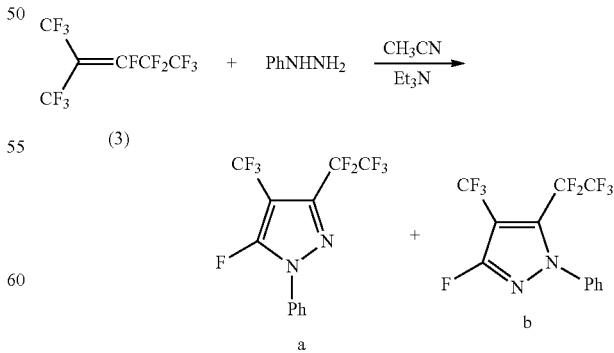

Furin et al Russian J. Org. Chem. 37 (2001) 11, 1621-1628 (Scheme 5) prepared a compound of formula (II) by reacting compound (3) with $PrCONHNH_2$:

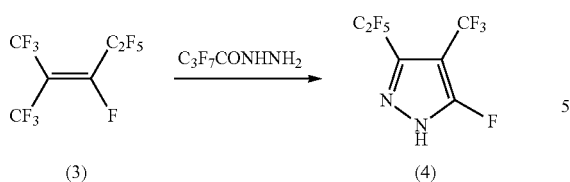

Wayne et al J. of Organic Chemistry 45 (1980) 3172-3176 (alkylation of unsubstituted pyrazole, page 3173 and 3174), Hase et al 37 (1904) Chemische Berichte, 3228-3238 (alkylation of piperidine, page 3233) and WO 2010/123999 (alkylation of unsubstituted pyrazole, pages 31 and 35) describe alkylation steps, however, they do not disclose an alkylation of a compound of formula (4), i.e. of a substituted pyrazole.

WO 2011012620 describes processes for the alcylation of pyrazoles.

EP 2 184 273 discloses a process for the preparation of a compound of formula (IV).

The problem to be solved by this invention was to identify a simple and selective process for preparing 5-fluoro-1H-pyrazoles from available fluoroalkenes and mono-substituted hydrazines, which should in particular be amenable for an industrial scale process. As an additional advantage, this process should have a favorable profile with respect to safety, e.g., replacement of hazardous monomethylhydrazin with less dangerous reagents (e.g. hydratzide), and production of unwanted waste material.

SUMMARY

A first aspect of the present invention refers to a process for the synthesis of 5-fluoro-1H-pyrazoles of the general formula (I)

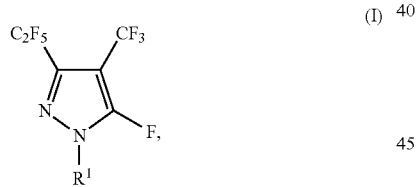

wherein $R^1$ represents $C_1$-$C_4$-alkyl, preferably methyl; comprising the steps of
  reacting intermediate (3) with $C_1$-$C_4$-alkyl-CONHNH$_2$ to prepare 3-perfluoroethyl-4-perfluoromethyl-5-fluoro-pyrazol (intermediate (4))

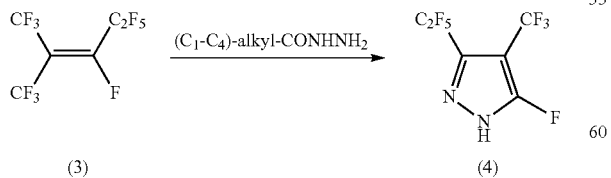

(herein referred to as step 3); and
reacting intermediate (4) with an $C_1$-$C_4$-alkylation agent, preferably a methylation agent to prepare a compound of formula (I) (herein referred to as step 4).

In a preferred embodiment of the first aspect of the present invention, the process is characterized by the steps of:
reacting hexafluoropropene (intermediate (1))

in the presence of a catalyst to form its dimer perfluoro-4-methyl-2-pentene (intermediate (2))

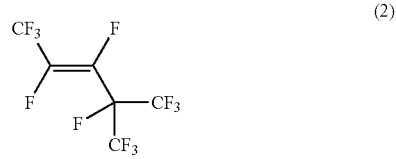

(herein referred to as step 1); and isomerizing perfluoro-4-methyl-2-pentene into perfluoro-2-methyl-2-pentene (intermediate (3))

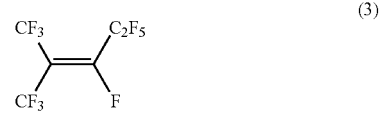

(herein referred to as step 2); and reacting a compound (3) with $C_1$-$C_4$-alkyl-CONHNH$_2$ to prepare 3-perfluoroethyl-4-perfluoromethyl-5-fluoro-pyrazol (intermediate (4))

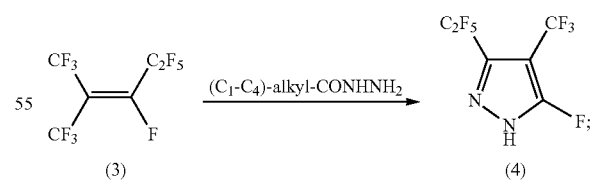

and reacting intermediate (4) with an ($C_1$-$C_4$)-alkylation agent, preferably a methylation agent, to prepare a compound of formula (I).

A further aspect refers to a process for the preparation of a compound of formula (IV)

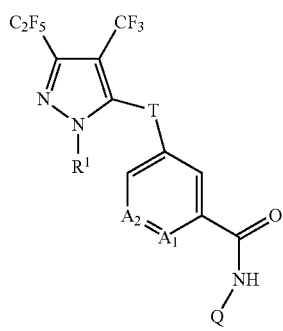

(IV)

in which
R¹ $C_1$-$C_4$-alkyl, preferably methyl; and
$A_1$ is C—R²; and
R² is hydrogen, fluorine, chlorine, bromine, CN, NO₂, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl, optionally halogenated $C_1$-$C_4$-alkylsulphinyl or N-cyclopropylaminocarbonyl (—C(=O)—NH—cyclopropyl); preferably hydrogen, fluorine, chlorine, bromine, CN, NO₂, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, NO₂, methyl, fluoromethyl, difluoromethyl, trifluoromethyl, 2,2,2-trifluoroethyl, methoxy, ethoxy, or pentafluoroethoxy, preferably hydrogen, fluorine, chlorine, bromine, most preferably chlorine; and
$A_2$ is C—R³ or nitrogen; and
R³ is hydrogen, methyl, fluorine or chlorine, preferably hydrogen; and
T represents one of the groups T1-T9 listed below, where the bond to the pyrazole head group [$N_2C_3R^1(C_2F)(CF_3)$] is marked with an asterisk *,

 T1

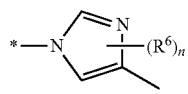 T2

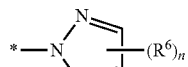 T3

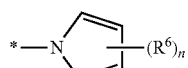 T4

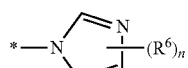 T5

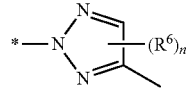 T6

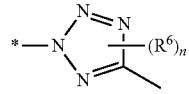 T7

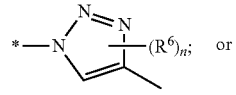 T8

*—C(=O)—NH—; T9 and
R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n represents the values 0-2, preferably 0, provided that n is 0 or 1 in T5, T6 and T8, and provided that n is 0 in T7; and
Q is hydrogen, cyano, hydroxy, formyl or one of the groupings $C_1$-$C_6$-alkyl, $C_3$-$C_6$-alkenyl, $C_3$-$C_6$-alkynyl, $C_3$-$C_9$-cycloalkyl, $C_3$-$C_9$-heterocycloalkyl, $C_1$-$C_4$-alkoxy, $C_4$-$C_{15}$-alkylcycloalkyl, $C_4$-$C_{15}$-cycloalkylalkyl, $C_1$-$C_6$-hydroxyalkyl, $C_6$-aryl-$C_1$-$C_3$-alkyl, $C_5$-$C_6$-heteroaryl$C_1$-$C_3$-alkyl, $C_1$-$C_4$-aminoalkyl, aminocarbonyl-$C_1$-$C_4$-alkyl or $C_1$-$C_4$-alkyl-amino-$C_1$-$C_4$-alkyl which are optionally substituted with one, two, three, four or five, preferably with one or two, more preferably with one, substituents independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and optionally independently with one, two or three substituents selected from the group consisting of halogen, cyano, nitro, hydroxycarbonyl, $C_1$-$C_2$-alkylcarbamoyl, $C_1$-$C_2$-alkyl, halogenated $C_1$-$C_2$-alkyl and $C_1$-$C_2$-alkoxy substituted phenyl; preferably Q is $C_3$-$C_6$-cycloalkyl, or $C_3$-$C_6$-cycloalkyl which is substituted with at least one substituent selected from the group consisting of chlorine, fluorine, bromine, iodine, cyano and hydroxy, or $C_6$-aryl-$C_1$-$C_3$-alkyl; more preferably cyclopropyl, 1-cyano-cyclopropyl or benzyl (—CH₂—C₆H₅);
comprising the steps as described above.

DETAILED DESCRIPTION OF A PREFERRED EMBODIMENT

One preferred embodiment refers to the process for the preparation of a compound of formula (IV) as described above, wherein a compound of formula (IV) is a compound of formula (II), preferably of formula (II').

Another preferred embodiment refers to the process for the preparation of a compound of formula (IV) described above, wherein a compound of formula (IV) is compound (IIa).

Another preferred embodiment refers to the process for the preparation of a compound of formula (IV), wherein the compound of formula (IV) is a compound of formula (II) as described herein, further comprising the steps of:

reacting compound (I) with a cyano-donor to prepare intermediate of formula (6)

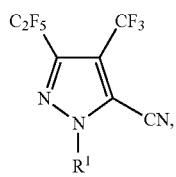

(6)

wherein
R¹ is optionally halogenated $C_1$-$C_4$-alkyl or optionally halogenated cyclopropyl, preferably methyl (herein referred to as Step 5); and
reacting compound (6) with an inorganic base in a first hydrolysis step followed by adding an inorganic acid in a second hydrolysis step to prepare intermediate of formula (7)

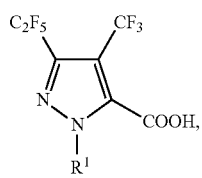

(7)

wherein R¹ is $C_1$-$C_4$-alkyl, preferably methyl (herein referred to as Step 6); and
reacting a compound of formula (8) or its salt (8') with an activated form (7') of compound (7)

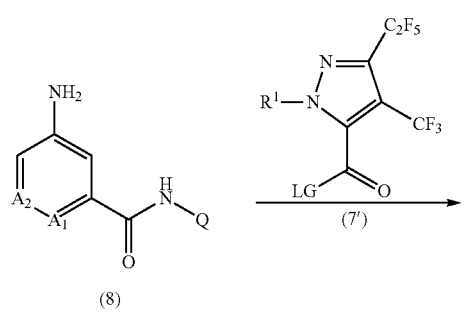

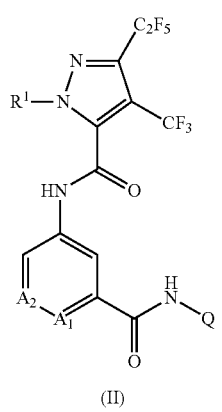

wherein R¹, $A_1$, $A_2$, and Q are as defined for compound (IV) and LG is any leaving group (herein referred to as Step 8),
to prepare a compound of formula (II).

Another preferred embodiment refers to the process for the preparation of a compound of formula (IV) described above, wherein a compound of formula (IV) is a compound of formula (III).

Another preferred embodiment refers to the process for the preparation of a compound of formula (III) wherein a compound of formula (III) is a compound of formula III', preferably compound (IIIa) or compound (IIIb).

Another preferred embodiment refers to the process for the preparation of a compound of formula (III), comprising the steps as described above further comprising the steps of reacting a compound of formula (I) with a compound of formula (11) by nucleophilic substitution of the fluoride at the ring position of a compound of formula (I) (herein referred to as Step 9)

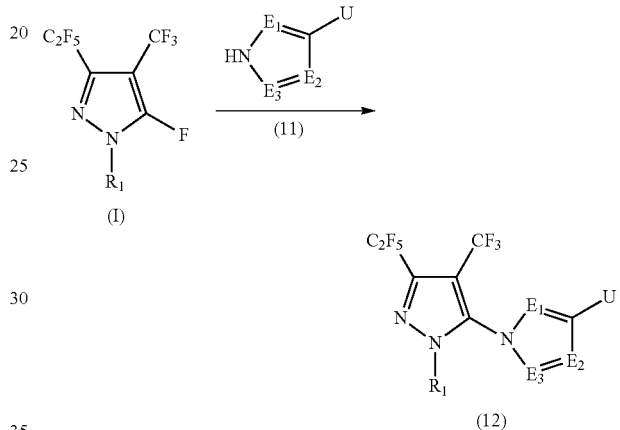

wherein $R_1$ is $C_1$-$C_4$-alkyl, preferably methyl; and
U represents bromine, iodine, triflate, boronic acid, boronic ester or trifluoroboronate; and
the five-membered cycles of $E_1$-$E_3$, carbon and nitrogen represent the 5-membered heterocycles selected from the group consisting of

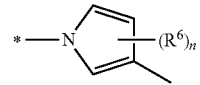

T1

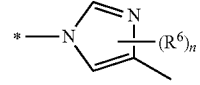

T2

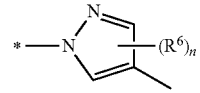

T3

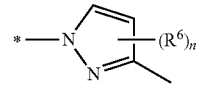

T4

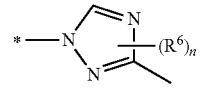

T5

-continued

T6
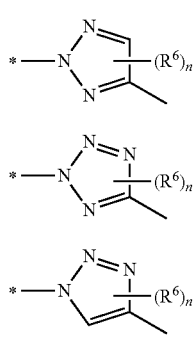

T7

T8 wherein
R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_5$-alkylsulphanyl, $C_1$-$C_6$-alkylsulphinyl, $C_1$-$C_6$-alkylsulphonyl, and
n represents the values 0-2, preferably 0, provided that n is 0 or 1 in T5, T6 and T8 and provided n is 0 in T7;
to prepare a compound of formula (12); and
reacting a compound of formula (12) and a compound of formula (13) (herein referred to as Step 10)

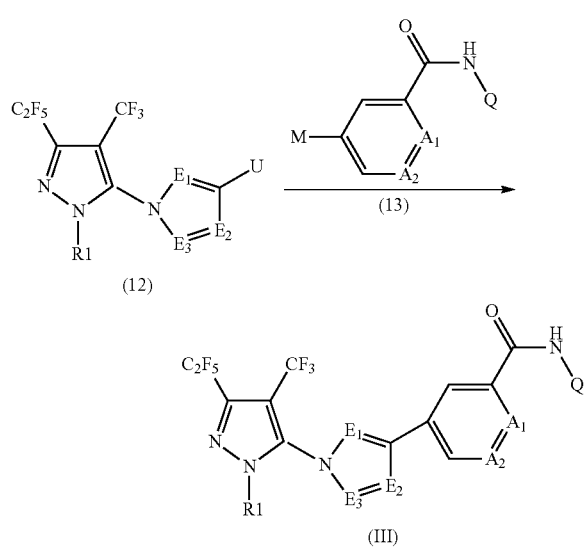

wherein $R^1$, $A_1$, $A_2$, and Q are as defined for a compound of formula (III) (or IV, respectively) and U and the five-membered cycles of $E_1$-$E_3$, carbon and nitrogen are as defined for compound (11); and
M represents bromine, iodine or triflate when U represents a boronic acid, boronic ester or trifluoroboronate; or
M represents a boronic acid, boronic ester or trifluoroboronate when U represents bromine, iodine or triflate;
to prepare a compound of formula (III).

Another preferred embodiment refers to the process for the preparation of a compound of formula (IV) as described above, wherein a compound of formula (IV) is a compound of formula (III''), preferably of formula (III''').

Another preferred embodiment refers to the process for the preparation of a compound of formula (III''), preferably of formula (III'''), as described above, characterized by the steps as described above, either optionally further comprising steps 9 and 10 as described above; or optionally further comprising the steps of
reacting a compound of formula (I) and an azide-donoer to prepare intermediate (14) (herein referred to as Step 11)

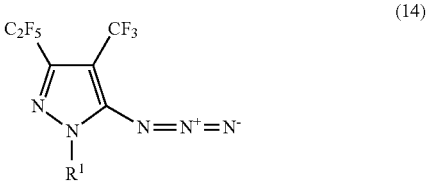

wherein $R^1$ is as defined for a compound of formula (III); and
reacting intermediate (14) with an intermediate of formula (15) to give an intermediate (III''*) (herein referred to as Step 12)

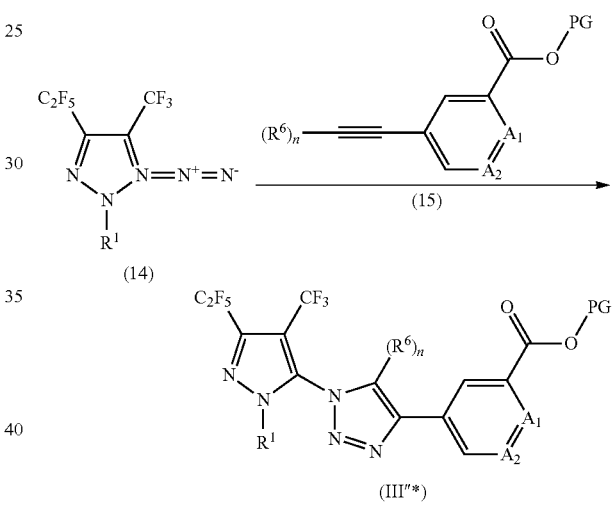

wherein $R^1$, $R^6$, $A_1$, and $A_2$ are as defined for compound (III), n is 0 or 1 and PG is any protective group of the carboxylic group such as $C_1$-$C_6$-alkyl (e.g., methyl).

Another preferred embodiment refers to a process as described above, wherein $R^1$ is methyl.

Another preferred embodiment refers to a process as described above, wherein the catalyst in Step 1 and the fluoride donor in Step 2 are identical.

Another preferred embodiment refers to any of the processes as described above, wherein step 3 and 4 are carried out in the same solvent, preferably acetonitrile or methylene chloride, more preferably methylene chloride.

Another preferred embodiment refers to a process as described above, wherein step 3 and 4 are carried out in the same solvent selected from the group consisting of acetonitrile or methylene chloride.

Use of intermediate (4) for the preparation of compound selected from the group consisting of a compound of formula (I), (6), (6a), (7), (7a), (I), (Ia), (II), (IIa), (III), (III'), (IIIa), (III''), (III'''), (IIIb), and (IV).

Another aspect refers to the use of a compound of formula (I), preferably of compound (Ia), prepared according to a process comprising the steps as described above for the preparation of a compound of formula (II).

Another aspect refers to the use of a compound of formula (I), preferably of compound (Ia), prepared according to a process comprising the steps as described above for the preparation of a compound of formula Another aspect refers to the use of a compound of formula (I), preferably of compound (Ia), prepared according to a process comprising the steps as described above for the preparation of a compound of formula (IV).

Definitions

The term "alkyl" as used herein refers to linear, branched or cyclic saturated hydrocarbyl groups. The definition $C_1$-$C_6$-alkyl encompasses the widest range defined herein for an alkyl group. Preferred alkyl are $C_1$-$C_4$-alkyl, more preferred $C_1$-$C_3$-alkyl, even more preferred $C_1$-$C_2$-alkyl. Specifically, this definition encompasses, for example, the meanings of methyl, ethyl, n-, isopropyl, n-, iso-, sec- and t-butyl, n-pentyl, n-hexyl, 1,3-dimethylbutyl and 3,3-dimethylbutyl.

The term "cycloalkyl" as used herein refers to a monocyclic, saturated hydrocarbyl group having 3 to 9 ($C_3$-$C_9$-cycloalkyl) and preferably 3 to 6 carbon ring members ($C_3$-$C_6$-cycloalkyl), for example (but not limited to) cyclopropyl, cyclopentyl and cyclohexyl. This definition also applies to cycloalkyl as part of a composite substituent, for example cycloalkylalkyl etc., unless defined elsewhere.

The term "halogen" as used herein refers to elements of the $7^{th}$ main group of the periodic table and their radicals, preferably fluorine, chlorine, bromine and iodine and their radicals. More Preferable halogens are chlorine and fluorine.

The term "halogenated alkyl" or "halogenated cyclopropyl" or other "halogenated" groups or similar "halogenated" groups as used herein refer to alkyl/cycloalkyl/cyclopropyl etc. moieties, wherein at least one (1) hydrogen atom attached to a carbon atom is replaced by a halogen, preferably selected from F, Cl, I, or Br, more preferably selected from F or $C_1$. Thus, the halogenated form of an alkyl moiety which has n carbon atoms and, thus, 2n+1 hydrogen, may have between 1 and 2n+1 halogen substitutions, i.e. 1, 2, or 3 hydrogen of a methyl moiety are each replaced by a halogen, 1, 2, 3, 4 or 5 hydrogen of an ethyl moiety are each replaced by a halogen, 1, 2, 3, 4, 5, 6 or 7 hydrogen of a propyl moiety are each replaced by a halogen, or 1, 2, 3, 4, 5, 6, 7, 8 or 9 hydrogen of a butyl moiety are each replaced by a halogen. In one preferred embodiment, all hydrogen of an alkyl moiety are replaced by halogen (perhalogenated moiety). More preferably, all halogen of a perhalogenated moiety are selected from $C_1$ or F or a combination thereof. Even more preferably, all hydrogen of an alkyl moiety are replaced by F. Thus, the halogenated form of a cyclopropyl moiety having 5 hydrogen may have 1, 2, 3, 4 or 5 halogen substitutions, preferably selected from F or $C_1$ or combinations thereof, more preferably the moiety is perfluorinated cyclopropyl.

According to the invention, "alkoxy" is straight-chain or branched —O-alkyl, preferably having 1 to 6 or even 1 to 4 carbon atoms, such as, for example, methoxy, ethoxy, n-propoxy, isopropoxy, n-butoxy, isobutoxy, sec-butoxy and tert-butoxy. Is also preferably alkoxy groups having 1 to 4 carbon atoms.

According to the invention, "heterocycloalkyl" is a carbocyclic ring system with at least one ring in which at least one carbon atom is replaced by a heteroatom, preferably by a heteroatom from the group consisting of N, O, S, P, B, Si, Se and which is saturated, unsaturated or heteroaromatic where the bonding to the core structure of a compound described herein is localized on a ring atom. Unless defined otherwise, the heterocyclic ring comprises preferably 3 to 9 ring atoms, in particular 3 to 6 ring atoms, whereof 1 to 5 ringatoms are carbon atoms provided that one or more, preferably 1 to 4, in particular 1, 2 or 3, ringatoms are heteroatoms in the heterocyclic ring. Preferably, a heteroringatom is selected from the group consisting of N, O and S, where, however, two oxygen atoms should not be directly adjacent. The heterocyclic rings usually comprise not more than 4 nitrogen atoms, and/or not more than 2 oxygen atoms and/or not more than 2 sulphur atoms. If the heterocyclyl radical or the heterocyclic ring is optionally substituted, it can be fused with other carbocyclic or heterocyclic rings. In the case of optionally substituted heterocyclyl, the invention also encompasses polycyclic systems such as, for example, 8-azabicyclo[3.2.1]octanyl or 1-azabicyclo[2.2.1]heptyl. In the case of optionally substituted heterocyclyl, the invention also encompasses spirocyclic systems, such as, for example, 1-oxa-5-azaspiro[2.3]hexyl.

According to the invention, "alkylcycloalkyl" is mono-, bi- or tricyclic cycloalkyl group which is substituted by one or more alkyl group(s), preferably wherein the sum of carbonatoms in the cycloalkyl and alkyl part of the substituent is between 4 to 15 or 4 to 9 carbon atoms, such as, for example, ethylcyclopropyl, isopropylcyclobutyl, 3-methylcyclopentyl and 4-methylcyclohexyl. Is also preferably alkylcycloalkyls having 4, 5 or 7 carbon atoms, such as, inter alia, ethylcyclopropyl or 4-methylcyclohexyl. Preferably, the alkylpart of an alkylcyclyoalkyl substituent is $C_1$ or a $C_2$ alkyl (—$CH_3$ or —$C_2H_5$).

According to the invention, "cycloalkylalkyl" is an alkyl group which is substituted by one or more mono-, bi- or tricyclic cycloalkyl group(s), preferably wherein the sum of carbonatoms in the cycloalkyl and alkyl part of the substituent is between 4 to 15, more preferably between 4 to 9 carbon atoms, such as, for example, cyclopropylmethyl, cyclobutylmethyl, cyclopentylmethyl, cyclohexylmethyl and cyclopentylethyl. Is also preferably cycloalkylalkyls having 4, 5 or 7 carbon atoms such as, inter alia, cyclopropylmethyl or cyclobutylmethyl. Preferably, the alkylpart of a cyclyoalkylalkyl substituent is $C_1$ or a $C_2$ alkylene (—$CH_2$— or —$C_2H_4$—).

According to the invention, "aryl" is an aromatic hydrocarbyl group (aryl). Preferably, an aryl group refers to $C_6$-$C_{14}$-aryl, i.e. an aryl group having between 6 and 14 carbon ring atoms. Also according to the invention "heteroaryl" refers to an aromatic group comprising at least one heteroatom ring atom individually selected from the group consisting of O, N, P and S (e.g., 1, 2, 3, 4 or even more heteroatom ring atom(s) although heteroaryl with 1, 2, 3 or 4 heteroatom ring atom are preferred). The definition $C_5$-$C_{14}$-heteroaryl refers to an aryl group comprising at least one heteroatom ring atom individually selected from the group consisting of O, N, P and S while the sum of ring atoms, including the at least one heteroatom ring atom as defined above, is between 5 and 14. For example, the term $C_5$-heteroaryl includes furane (1 oxygen ring atom and 4 carbon ring atoms) or imidazole (2 nitrogen ring atoms and 3 carbon ring atoms). More preferred aryl compounds are $C_6$-aryl, $C_5$-heteroaryl or $C_6$-heteroaryl. Examples are phenyl, cycloheptatrienyl, cyclooctatetraenyl, naphthyl and anthracenyl; 2-furyl, 3-furyl, 2-thienyl, 3-thienyl, 2-pyrrolyl, 3-pyrrolyl, 3-isoxazolyl, 4-isoxazolyl, 5-isoxazolyl, 3-isothiazolyl, 4-isothiazolyl, 5-isothiazolyl, 3-pyrazolyl, 4-pyrazolyl, 5-pyrazolyl, 2-oxazolyl, 4-oxazolyl, 5-oxazolyl, 2-thiazolyl, 4-thiazolyl, 5-thiazolyl, 2-imidazolyl, 4-imidazolyl, 1,2,4-oxadiazol-3-yl, 1,2,4-oxadiazol-5-yl, 1,2,4-thiadiazol-3-yl, 1,2,4-thiadiazol-5-yl, 1,2,4-triazol-3-yl, 1,3,4-oxadiazol-2-yl, 1,3,4-thiadiazol-2-yl and 1,3,4-triazol-2-yl; 1-pyrrolyl, 1-pyrazolyl, 1,2,4-triazol-1-yl, 1-imidazolyl, 1,2,3-triazol-1-yl, 1,3,4-triazol-1-yl; 3-pyridazinyl, 4-pyridazinyl, 2-pyrimidinyl, 4-pyrimidinyl, 5-pyrimidinyl, 2-pyrazinyl, 1,3,5-triazin-2-yl and 1,2,4-triazin-3-yl.

According to the invention, "Arylalkyl" and "heteroarylalkyl" is an alkyl group (alkylene chain) which is substituted by one or more aryl group(s) or one or more heteroaryl group(s), respectively. The alkylene chain has preferably between 1 and 6 carbon atoms ($C_1$-$C_6$-alkylene chain), preferably between 1 and 3 carbon atoms. The definition $C_7$-$C_{20}$-arylalkyl group encompasses the widest range defined herein for an arylalkyl group having a total of 7 to 20 atoms in the combination of aryl ring system and the alkylene chain. Preferred arylalkyls are $C_7$-$C_9$-arylalkyl, e.g., $C_6$-aryl-$C_1$-$C_3$-alkyl such as benzyl (—$CH_2$—$C_6H_5$), phenylethyl (—$CH_2$—$CH_2$—$C_6H_5$) or phenylpropyl (—$(CH_2)_3$—$C_6H_5$). The definition $C_{6-20}$-heteroarylalkyl group encompasses the widest range defined herein for an heteroarylalkyl group having a total of 6 to 20 atoms in the combination of heteroaryl ring system and the alkylene chain, wherein at least 1 ring atom in the heteroaryl ring system is a heteroatom. Preferred heteroarylalkyls are $C_6$-$C_9$-arylalkyl, e.g., $C_5$-heteroaryl-$C_1$-$C_3$-alkyl such as pyrrol-2-yl-methyl (—$CH_2$—$C_4NH_4$) or $C_6$-heteroaryl-$C_1$-$C_3$-alkyl such as 2-pyridin-2-yl-methyl (—$CH_2$—$C_5NH_4$).

According to the invention, "Alkylaryl" is an aryl group which is substituted by one or more alkyl group(s), preferably $C_1$-$C_6$-alkyl group(s), more preferably $C_1$-$C_3$-alkyl group(s). The definition $C_7$-$C_{20}$-alkylaryl group encompasses the widest range defined herein for an alkylaryl having a total of 7 to 20 atoms in the aryl ring system and alkyl group(s), preferably $C_7$-$C_9$-alkylaryl, such as $C_1$-$C_3$-alkyl-$C_6$-aryl. Specifically, this definition encompasses, for example, the meanings of tolyl (—$C_6H_4$—$CH_3$), ethylphenyl (—$C_6H_4$—$C_2H_5$), or 2,3-, 2,4-, 2,5-, 2,6-, 3,4- or 3,5-dimethylphenyl.

Similarly, an "alkylheteroaryl" group is a heteroaryl group as defined herein which is substituted by one or more alkyl group(s). The definition $C_6$-$C_{20}$-alkylheteroaryl group encompasses the widest range defined herein for an alkylheteroaryl having a total of 6 to 20 atoms in the heteroaryl ring system and alkyl group(s), which individually are preferably $C_1$-$C_6$-alkyl group(s), more preferably $C_1$-$C_3$-alkyl group(s). Preferably alkylheteroalkyl is $C_6$-$C_9$-alkylheteroaryl. For example, $C_1$-$C_3$-alkyl-$C_6$-heteroaryl, such as 2-methyl-pyridyl (—$C_5NH_3$—$CH_3$), 2-ethyl-pyridyl, 2,3-dimethyl-pyridyl or 2-methyl-3-ethyl-pyridyl.

According to the invention, "alkylcarbonyl" is a straight-chain or branched alkyl-C(=O), preferably having 2 to 7 carbon atoms (—C(=O)—$C_1$-$C_6$-alkyl), such as methylcarbonyl, ethylcarbonyl, n-propylcarbonyl, isopropylcarbonyl, sec-butylcarbonyl and tert-butylcarbonyl. Preferable alkylcarbonyls have 1 to 4 carbon atoms ($C_1$-$C_3$-alkyl-C(=O)).

According to the invention, "alkylaldehyde" is a straight-chain or branched alkyl substituted with a C(=O)H group (-alkyl-CH(=O)), preferably having 2 to 7 carbon atoms (—$C_1$-$C_6$-alkyl-CH(=O)). Preferable alkylcarbonyls have 2 to 4 carbon atoms (—$C_1$-$C_3$-alkyl-CH(=O)).

According to the invention, "aminoalkyl", "alkylaminoalkyl" (secondary amine) and "aminocarbonylalkyl", respectively, refer to amino (—$NH_2$), aminoalkyl (—NHalkyl) and (—C(=O)—$NH_2$), respectively, substituted alkylene chains. Preferably, alkyl in the three listed amino substituents is $C_1$-$C_6$-alkyl, more preferably $C_1$-$C_4$-alkyl, e.g., $C_1$-alkylamino refers to —$CH_2$—$NH_2$, $C_1$-alkylamino-$C_1$-alkyl refers to —$CH_2$—NH—$CH_3$, and $C_1$-alkylcarbonylamino refers to —$CH_2$—C(=O)—$NH_2$.

"Optionally substituted" groups as used herein are preferably substituted by 1, 2, 3, 4, 5, preferably by 1 or 2 independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and phenyl.

The person skilled in the art is aware that the terms "a" or "an", as used in the present application, may, depending on the situation, mean "one (1)" "one (1) or more" or "at least one (1)".

Not included herein are chemical structures and combinations of embodiments which are against natural laws and which the person skilled in the art would therefore exclude based on his/her expert knowledge. Ring structures having three or more adjacent oxygen atoms, for example, are excluded.

"Intermediate" as used herein describes the substances which occur in the process according to the invention and are prepared for further chemical processing and are consumed or used therein in order to be converted to another substance. The intermediates can often be isolated and intermediately stored or are used without prior isolation in the subsequent reaction step. The term "intermediate" also encompasses the generally unstable and short-lived intermediates which occur transiently in multistage reactions (staged reactions) and to which local minima in the energy profile of the reaction can be assigned.

The inventive compounds may be present as mixtures of any different isomeric forms possible, especially of stereoisomers, for example E and Z isomers, threo and erythro isomers, and optical isomers, but if appropriate also of tautomers. Both the E and the Z isomers are disclosed and claimed, as are the threo and erythro isomers, and also the optical isomers, any mixtures of these isomers, and also the possible tautomeric forms.

DETAILED DESCRIPTION

In the following, the invention and various embodiments of the invention are described in more detail. It is obvious to the person skilled in the art that all embodiments can be present alone or in combination.

Surprisingly, 5-fluoro-1H-pyrazoles of the general formula (I)

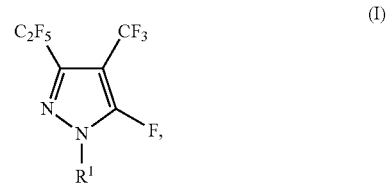

wherein $R^1$ is $C_1$-$C_4$-alkyl, preferably methyl, can be prepared in high purity and in a short and simple process by reacting a compound (3) with $C_1$-$C_4$-alkyl-CONHNH$_2$ to prepare 3-perfluoroethyl-4-perfluoromethyl-5-fluoro-pyrazol (intermediate (4)) and further reacting intermediate (4) with an $C_1$-$C_4$-alkylation agent, preferably a methylation agent, to prepare a compound of formula (I):

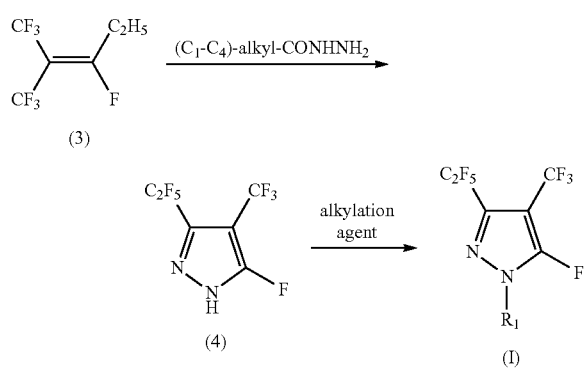

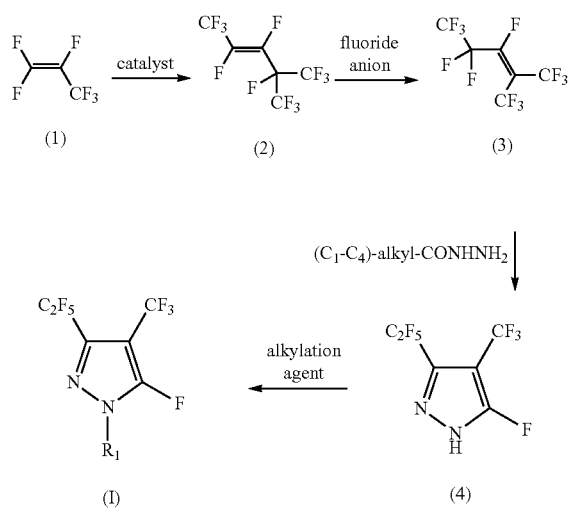

wherein $R^1$ represents $C_1$-$C_4$-alkyl, preferably methyl.

Wayne et al J. of Organic Chemistry 45 (1980) 3172-3176 (alkylation of unsubstituted pyrazole, page 3173 and 3174), Hase et al 37 (1904) Chemische Berichte, 3228-3238 (alkylation of piperidine, page 3233) and WO 2010/123999 (alkylation of unsubstituted pyrazole, pages 31 and 35) describe alkylation steps. However, Alkylation of unsymmetrically substituted pyrazoles usually proceeds with formation of two regioisomers. The composition of the mixture depends on the nature of substrate, alkylating reagents and reaction conditions. Surprisingly, the alkylation of this electron poor pyrazol proceed with good yield and high regioselectivity (see, e.g., WO 2011012620).

In one preferred embodiment, 5-fluoro-1H-pyrazoles of the general formula (I) can be prepared in high purity and in a short and simple process by reacting hexafluoropropene (intermediate (1)) to perfluoro-4-methyl-2-pentene (intermediate (2)), isomerizing intermediate (2) to perfluoro-2-methyl-2-pentene (intermediate (3)), reacting intermediate (3) with $C_1$-$C_4$-alkyl-CONHNH$_2$ to prepare 3-perfluoroethyl-4-perfluoromethyl-5-fluoro-pyrazol (intermediate (4)) and further reacting intermediate (4) with an $C_1$-$C_4$-alkylation agent, preferably a methylation agent, to prepare a compound of formula (I):

The terms "catalyst" and "alkylation agent" are as defined above.

Step 1: Dimerisation of Hexafluoropropen

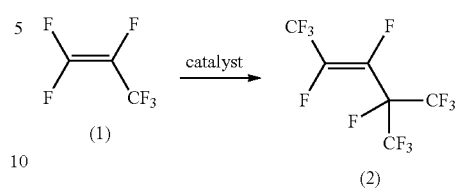

Typically, the reaction is carried out in the presence of a catalyst such as a fluoride (F) donor (e.g., Me$_4$N F, Bu$_4$N F, NaF, KHF$_2$, KF or CsF. Preferred catalysts are KHF$_2$, KF and CsF, more preferably KF or CsF.

Typical solvents are polar solvents like Glyme (glycolethers such as monoglycolether of formula $C_1$-$C_4$-alkylOCH$_2$CH$_2$OH or benzylOCH$_2$CH$_2$OH or phenylOCH$_2$CH$_2$OH, dialkylether of formula $C_1$-$C_4$-alkylOCH$_2$CH$_2$O—$C_1$-$C_4$-alkyl or esters $C_1$-$C_4$-alkylOCH$_2$CH$_2$OCOCH$_3$, preferably dimethoxyethane), acetonitrile, DMF (dimethylformamide), DMA (dimethylacetamide), N-methylpyrrolidone, sulfolane, benzonitrile, dimethoxyethan, diethyleglkykoldimethylether. Reaction temperature is between 10° C. and 50° C., preferably between 20° C. and 40° C.

Reaction time is depending of the reaction size and is typically between 1 min and 30 h.

Although purification steps for Dimer (2) and/or removal or exchange of solvent after Step 1 can occur before Step 2, Step 1 and Step 2 can be performed as a one pot reaction.

A "one pot reaction", as long as not stated otherwise, refers to two reaction steps (e.g. Step 3 and Step 4) which are carried out without interim purifying steps after the first reaction step and prior of performing the second step and/or without the need of exchanging solvent.

"Without purifying steps" as used in the present application refers to the absence of purifying steps selected from the group consisting of removal of more than 10% of the solvent of a reaction mixture by evaporation, e.g. under reduced pressure and/or heating, crystallization of an intermediate or compound resulting from a reaction step in a solvent different from the solvent of the reaction mixture, or chromatography.

"Exchanging solvent" as used in the present application means that no major amounts of a solvent of a different kind is added to a reaction mixture. "No major amount" refers to a volume of less than 50 vol % based on the volume of a solvent in a reaction mixture. For example, the addition of 5 ml acetonitrile to a reaction mixture comprising 200 ml methylene chloride is not an exchange of solvent even if part of the solvent of the reaction mixture, such as 50 vol % of the solvent of a reaction mixture, was removed by, e.g. phase separation. However, the addition of more than 100 ml of acetonitrile (solvent of a different kind) to a reaction mixture comprising 200 ml methylene chloride as solvent is considered an exchange of solvent even if methylene chloride is not removed prior to the addition of acetonitrile. Also considered as an exchange of solvent is the removal of at least 95 vol % of a first solvent (e.g. acetonitrile) in a reaction mixture after the first reaction step by, e.g., phase separation, followed by adding a solvent of a different kind, e.g., dichloromethane.

Although it is not mandatory, a one pot reaction is preferably carried out in the same reaction vessel.

Step 2: Isomerization of perfluoro-4-methyl-2-pentene (inactive Dimer) to perfluoro-2-methyl-2-pentene (2) →[fluoride anion]→ (3)

Typically, the isomerization is carried out in the presence of a fluoride donor.

NaF, KF, KHF$_2$, AlF$_3$ or CsF can be used in combination with an auxiliary catalyst comprises one or more of ethylenglykoldimethylether, sulfolane, 15-crown ether-5 and 18-crown ether-6, quaternary ammonium salts like (tetraalkylammonium fluorides, hydrodifluorides (e.g. alkaline hydrodifluorides such as KHF$_2$) hydrochloride or hydrobromide) or tetra-C$_1$-C$_6$-alkylphosphonium salts or tetraphenylphosphonium salts like Ph$_4$P Cl, Ph$_4$P Br, Ph$_4$P Br or Ph$_4$P HF$_2$.

Preferred fluoride donors are NaF, KF, KHF$_2$, CsF, AlF$_3$ more preferable KF.

Isomerization usually occurs at elevated temperature between 25 to 60° C. at normal pressure, but the reaction can be performed under pressure up to 6 bar and a temperature between 60 to 80° C.

Typically solvents are polar solvents like glyme, acetonitrile, DMF, DMA, benzonitrile, dimethoxyethane or diethylenglkykoldimethylether or combinations thereof. More preferable solvents are acetonitrile, DMF or DMA.

The reaction time is usually between 1 h and 10 h such as between 2 h and 8 h.

In one preferred embodiment, the solvent in Step 1 and Step 2 is the same, preferably acetonitrile.

In another preferred embodiment, Step 3 and Step 4 are reacted as a one-pot-reaction and the solvent in Step 3 and Step 4 is the same, preferably acetonitrile or methylene chloride, more preferably methylene chloride.

Although purification steps for intermediate (3) and/or exchange of solvent after Step 2 can occur before Step 3; Step 1 to Step 3; or Step 2 and Step 3 can be performed as a one pot reaction, i.e. without purifying steps for intermediate (2) and/or intermediate (3) prior of performing Step 3 and/or without the need of exchanging solvent prior of performing Step 2 and Step 3 or prior of performing Step 3, respectively.

Step 3: Reaction of perfluoro-2-methyl-2-pentene (3) with (C$_1$-C$_4$)-alkyl-CONHNH$_2$ (3) →[(C$_1$-C$_4$)-alkyl-CONHNH$_2$]→ (4)

Generally, the reaction is carried out in a solvent. Typical solvents are
- alkanes, like hexanes preferably cyclohexane or methylcyclohexane;
- haloalkanes, preferably dichlorometane, dichlorethane;
- alcohols, preferably methanol, ethanol, or isopropanol;
- nitriles, preferably acetonitrile, or butyronitrile;
- amides, preferably DMF, or dimethylacetamide;
- ethers preferably diethylether, methyltert.butylether, dimethoxyethane, diglym,
- benzene, toluene, dichlorobenzene, chlorobenzenes.

Most preferred solvents are CH$_3$CN, DMF, dichlormethane, ethanol.

The reaction temperature should range between 10 to 60° C., preferably between 20 to 40° C.

Typically, the reaction can be carried out under standard pressure (around 1,013 bar, e.g., between 0.7 and 1.3 bar). However, in the case of volatile regents like MeBr and MeI, the reaction can also be carried out under higher pressure such as between 2 to 6 bar.

Typically, the ratio between intermediate (3) and the Acylhydrazine is between 1:1 and 1:2, preferably between 1:1.3 and 1:1.5.

Preferably, the C$_1$-C$_4$-alkyl-CONHNH$_2$ is C$_3$H$_7$—CONHNH$_2$.

The Reaction time is not of critical importance and can depend on the reaction volume, preferably, it is within the range of 1 h to 10 h, more preferably within the range of 1 h to 5 h.

Although purification steps for intermediate (4) and/or removal or exchange of solvent after Step 3 can occur before Step 4, Step 1 to Step 4 or Step 2 to Step 4 or Step 3 and Step 4 can be performed as a one pot reaction, i.e. without purifying steps for dimer (2) and/or intermediate (3) and/or intermediate (4) prior of performing Step 4 and/or without the need of removing or exchanging solvent prior of performing Step 4.

Step 4: Reaction of Intermediate (4) with an Alkylation Agent

The reaction of intermediate (4) with a C$_1$-C$_4$-alkylation agent, preferably a methylation agent, to prepare a compound of formula (I) is herein referred to as step 4.

Typical alkylation agents are alkyl bromides, alkyl iodides or dialkylsulphates or trialkylphosphates such as CH$_3$Cl, CH$_3$Br, CH$_3$I, (CH$_3$)$_2$SO$_4$ or (CH$_3$O)$_3$PO. In one preferred embodiment, the alkylation agent is CH$_3$Br, CH$_3$I, (CH$_3$)$_2$SO$_4$.

Typically, the ratio between intermediate (4) and the alkylation agent is between 1:1 and 1:2, preferably between 1:1.1 and 1:1.5.

The alkylation reaction can be performed in different solvents such as
- alkanes, like hexanes e.g. cyclohexane or methylcyclohexane;
- haloalkanes, preferably dichlorometane, dichlorethane;
- alcohols, preferably methanol, ethanol, or isopropanol;
- nitriles, preferably acetonitrile, or butyronitrile;
- amides, preferably dimethylformamide, or dimethylacetamide;
- ethers like diethylether, methyltert.butylether, dimethoxyethane, diglym,
- benzene, toluene, dichlorobenzene, chlorobenzenes
- lactams such as N-methylpyrrolidone (NMP).

Most preferred solvents are dimethylformamide (DMF), N-methylpyrrolidone (NMP), dichloromethane (CH$_2$Cl$_2$) or acetonitrile (CH$_3$CN).

In one preferred embodiment, the alkylation reaction is carried out in the presence of an organic or inorganic weak base. Preferred bases are Li$_2$CO$_3$, Na$_2$CO$_3$, K$_2$CO$_3$, NEt$_3$.

Generally, the reaction time is not of critical importance and can depend on the reaction volume, the reactivity of the alkylation reagents, preferably, it is within the range of 3 h to 20 h, more preferably within the range of 1 h to 5 h.

Usually, the alkylation occurs at normal pressure, e.g., at around standard pressure (around 1,013 bar, e.g., between 0.7 and 1.3 bar). However, in the case of volatile reagents like CH$_3$Br, the reaction can also be carried out under higher pressure such as between 2 to 6 bar.

A particularly preferred embodiment of the present invention relates to a process for preparing compound of formula (Ia)

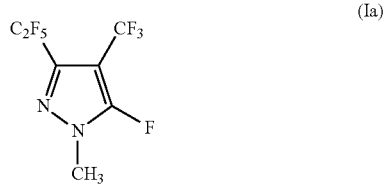

starting from perfluoro-2-methyl-2-pentene (3) or hexafluoropropen (1) comprising the steps described herein above.

Step 5

In a Step 5, the compound of formula (I), preferably compound (Ia), can be transformed into its CN analog of formula (6) or (6a), respectively

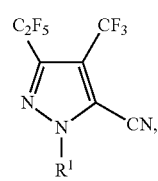

wherein R$^1$ is (C$_1$-C$_4$)-alkyl, preferably, a compound of formula (6) is a compound of formula (6a):

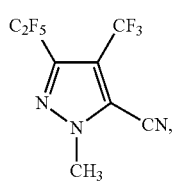

by reacting compound (I), preferably compound (Ia), with a CN-donor such as alkaline cyanides (e.g., NaCN, KCN, CsCN, or CuCN).

Typical solvents are acetonitrile, DMF, DMA, N-methylpyrrolidone (NMP), Sulfolan, dimethoxyethane, diglym. Preferred solvents are acetonitrile, DMF or DMA.

Typically, the temperature for this reaction is between 30° C. and 120° C., preferably between 40° C. and 110° C., more preferably above 60° C. such as between 60° C. and 120° C. or between 60° C. and 100° C.

Generally, the reaction time is not of critical importance and can depend on the reaction volume. Preferably, the reaction time is between 2 h and 8 h, more preferably between 4 and 8 h.

Step 6

In a Step 6, a compound of formula (6), preferably (6a), can be transformed in its carboxylic acid analog of formula (7), preferably formula (7a), respectively, according to hydrolysis steps known in the art:

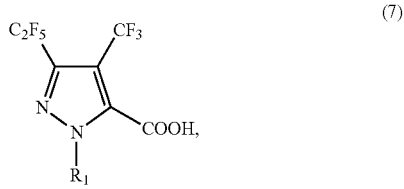

wherein R$^1$ is C$_1$-C$_4$-alkyl, preferably a compound of formula (7) is a compound of formula (7a):

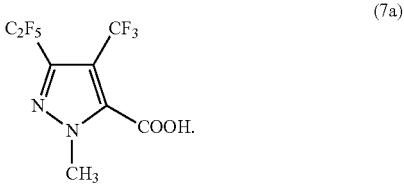

The conversion of a cyano group (—CN) into a carboxylic group (—COOH) is generally performed under acidic or basic conditions.

For acidic hydrolysis, preference is given to mineral acids, for example H$_2$SO$_4$, HCl, HSO$_3$Cl, HF, HBr, HI, H$_3$PO$_4$ or organic acids, for example CF$_3$COOH, p-toluenesulphonic acid, methanesulphonic acid, trifluoromethanesulphonic acid. The reaction can be accelerated by the addition of catalysts, for example FeCl$_3$, AlCl$_3$, BF$_3$, SbCl$_3$, NaH$_2$PO$_4$. The reaction can likewise be performed without addition of acid, only in water.

Basic hydrolysis is effected in the presence of inorganic bases such as alkali metal hydroxides, for example lithium hydroxide, sodium hydroxide or potassium hydroxide, alkali metal carbonates, for example Na$_2$CO$_3$, K$_2$CO$_3$ and alkali metal acetates, for example NaOAc, KOAc, LiOAc, and alkali metal alkoxides, for example NaOMe, NaOEt, NaOt-Bu, KOt-Bu of organic bases such as trialkylamines, alkylpyridines, phosphazenes and 1,8-diazabicyclo[5.4.0]undecene (DBU). Preference is given to the inorganic bases, for example NaOH, KOH, Na$_2$CO$_3$ or K$_2$CO$_3$. To generate the protonated acidic form of formula (7) or (7a), respectively, a following step of acidification should follow.

Typically, suitable inorganic acids for performing the acidification after completion of the basic hydrolysis is any acid which is stronger than the deprotonated form of a compound of formula (7) or (7a), respectively. Preference is given to mineral acids, for example H$_2$SO$_4$, HCl, HF, HBr, HI, H$_3$PO$_4$ or organic acids, for example CF$_3$COOH, p-toluenesulphonic acid, methanesulphonic acid, trifluoromethanesulphonic acid. Preferred acids for this acidifications are HCl or H$_2$SO$_4$.

The reaction step can be performed in substance or in a solvent. Preference is given to performing the reaction in a solvent. Suitable solvents are, for example, selected from the group comprising water, alcohols such as methanol, ethanol, isopropanol or butanol, aliphatic and aromatic hydrocarbons, for example n-hexane, benzene or toluene, which may be substituted by fluorine and chlorine atoms, such as methylene chloride, dichloroethane, chlorobenzene or dichlorobenzene; ethers, for example diethyl ether, diphenyl ether, methyl tert-butyl ether, isopropyl ethyl ether, dioxane, diglyme, dimethylglycol, dimethoxyethane (DME) or THF; nitriles such as methyl nitrile, butyl nitrile or phenyl nitrile; amides we dimethylformamide (DMF) or N-methylpyrrolidone or mixtures of such solvents, particular preference being given to water, acetonitrile, dichloromethane and alcohols (ethanol). Preferably, the reaction is carried out in water. The process step of the invention is generally performed under standard pressure. Alternatively, however, it is also possible to work under vacuum or under elevated pressure (for example reaction in an autoclave with aqueous HCl).

The reaction time may, according to the batch size and the temperature, be selected within a range between 1 hour and several hours such as between 1 h and 30 h, preferably between 3 h and 20 h.

Preference is given to conversion by means of basic hydrolysis followed by an acidification.

The process step of the invention is performed preferably within a temperature range from 20° C. to 150° C., more preferably at temperatures of 30° C. to 110° C., most preferably at 30° C. to 80° C.

Generally the reaction time may, according to the batch size and the temperature, be selected within a range between 1 hour and several hours such as between 1 h and 30 h, preferably between 3 h and 20 h.

Compounds of Formula (II)

The present invention also refers to a process to produce an insecticidal compound of formula (II), preferably of formula (II'), more preferably of formula (IIa), based on the preparation of compounds of formula (I). Compounds of formula (II) are, e.g., known from WO 2010/051926.

nated C$_1$-C$_4$-alkoxy, optionally halogenated C$_1$-C$_4$-alkylsulphonyl, optionally halogenated C$_1$-C$_4$-alkylsulphinyl or N-cyclopropylaminocarbonyl (—C(=O)—NH—cyclopropyl); preferably hydrogen, fluorine, chlorine, bromine, CN, NO$_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, NO$_2$, methyl, fluoromethyl, difluoromethyl, trifluoromethyl, 2,2,2-trifluoroethyl, methoxy, ethoxy, or pentafluoroethoxy, preferably hydrogen, fluorine, chlorine, bromine, most preferably chlorine; and A$_2$ is C—R$^3$ or nitrogen; and R$^3$ is hydrogen, methyl, fluorine or chlorine, preferably hydrogen; and Q is hydrogen, cyano, hydroxy, formyl or one of the groupings C$_1$-C$_6$-alkyl, C$_3$-C$_6$-alkenyl, C$_3$-C$_6$-alkynyl, C$_3$-C$_9$-cycloalkyl, C$_3$-C$_9$-heterocycloalkyl, C$_1$-C$_4$-alkoxy, C$_4$-C$_{15}$-alkylcycloalkyl, C$_4$-C$_{15}$-cycloalkylalkyl, C$_1$-C$_6$-hydroxyalkyl, C$_6$-aryl-C$_1$-C$_3$-alkyl, C$_5$-C$_6$-heteroaryl-C$_1$-C$_3$-alkyl, C$_1$-C$_4$-aminoalkyl, aminocarbonyl-C$_1$-C$_4$-alkyl or C$_1$-C$_4$-alkyl-amino-C$_1$-C$_4$-alkyl which are optionally substituted with one, two, three, four or five, preferably with one or two, more preferably with one, substituents independently selected from the group consisting of hydroxy, nitro, amino, halogen, C$_1$-C$_3$-alkoxy, cyano, hydroxycarbonyl, C$_1$-C$_4$-alkoxycarbonyl, C$_1$-C$_4$-alkylcarbamoyl, C$_4$-C$_6$-cycloalkylcarbamoyl and optionally independently with one, two or three substituents selected from the group consisting of halogen, cyano, nitro, hydroxycarbonyl, C$_1$-C$_2$-alkylcarbamoyl, C$_1$-C$_2$-alkyl, halogenated C$_1$-C$_2$-alkyl and C$_1$-C$_2$-alkoxy substituted phenyl; preferably Q is C$_3$-C$_6$-cycloalkyl, or C$_3$-C$_6$-cycloalkyl which is substituted with at least one substituent selected from the group consisting of chlorine, fluorine, bromine, iodine, cyano and hydroxy, or C$_6$-aryl-C$_1$-C$_3$-alkyl; more preferably cyclopropyl, 1-cyano-cyclopropyl or benzyl (—CH$_2$—C$_6$H$_5$);

preferably, a compound of formula (II) is a compound of formula (II'):

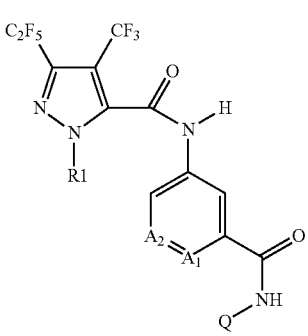

(II)

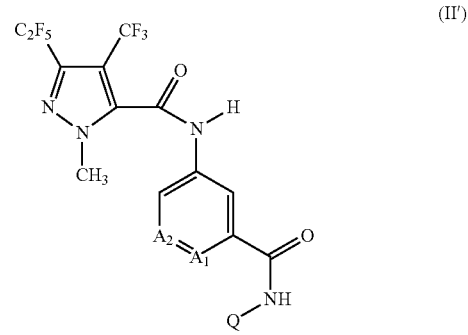

(II')

wherein
R$^1$ is C$_1$-C$_4$-alkyl, preferably methyl; and
A$_1$ is C—R$^2$; and
R$^2$ is hydrogen, fluorine, chlorine, bromine, CN, NO$_2$, optionally halogenated C$_1$-C$_6$-alkyl, optionally halogewherein A$^1$ and A$^2$ and Q are as defined for a compound of formula (II), characterized in that the process comprises steps 3 and 4 as described above.

In one preferred embodiment, the compound of formula (II) is compound (IIa) defined by the following substituents:

| R¹  | A₂  | A₁   | Q      |
|-----|-----|------|--------|
| CH₃ | C—H | C—Cl | Benzyl |

The new and inventive process for preparing a compound of formula (II), preferably (II'), more preferably (IIa), is characterized in that the process comprises steps 3 and 4 as described above. In one preferred embodiment, the process is characterized in that it comprises steps 1 to 4 described above. In another preferred embodiment, the process comprises in addition to steps 3 and 4 or in addition to steps 1 to 4 optionally Step 5 and Step 6 as described above and optionally, by the subsequent Step 8 described below. Optionally, compound (8) in Step 8 can be produced by the reaction indicated in Step 7 which is described below:

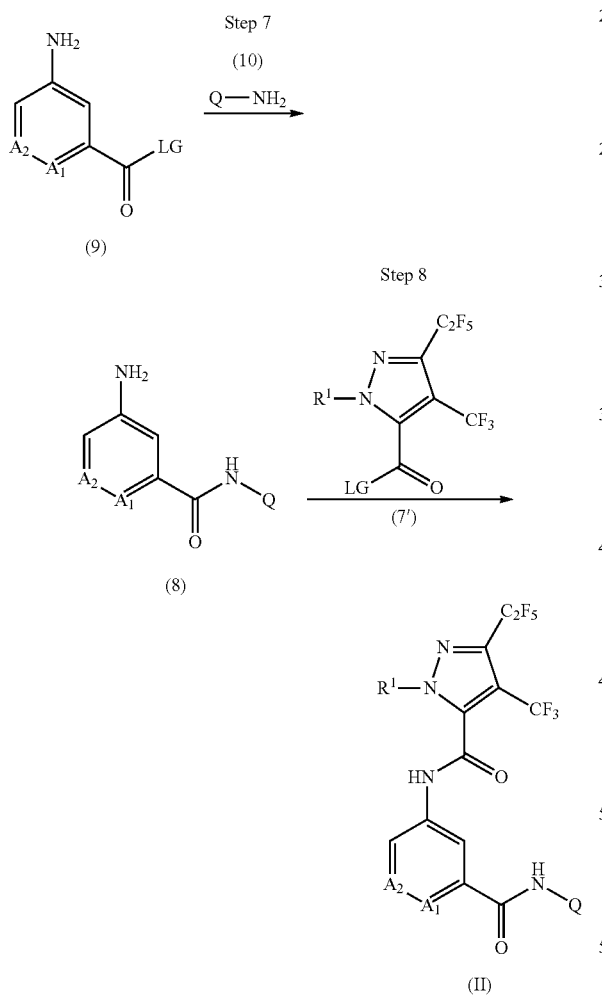

wherein R¹ and A₁ and A₂ and Q have the meanings described for compounds of formula (II). LG is any desired leaving group, e.g. halogen or anhydrate.

Typically, an amine derivative of the formula (8) does not only refer to the amine but also to its salt form (8)H⁺W⁻ wherein W⁻ is selected from ⁻, Cl⁻, Br⁻, J⁻, HSO₄⁻, CH₃COO⁻, BF₄⁻, CH₃SO₃⁻, Toluensulphonic acid, CF₃COO⁻ or CF₃SO₃⁻.

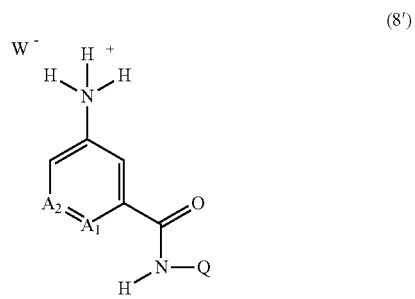

wherein W⁻ is selected from ⁻, Cl⁻, Br⁻, J⁻, HSO₄⁻, CH₃COO⁻, BF₄⁻, CH₃SO₃⁻, Toluensulphonic acid, CF₃COO⁻ or CF₃SO₃⁻.

Thus, one preferred embodiment refers to the reaction of Step 8 wherein the compound of formula (8) is present in its salt form (8)H⁺W⁻, wherein W⁻ is selected from ⁻, Cl⁻, Br⁻, J⁻, HSO₄⁻, CH₃COO⁻, BF₄⁻, CH₃SO₃⁻, Toluensulphonic acid, CF₃COO⁻ or CF₃SO₃⁻.

In one more preferred embodiment, a compound of formula (8) is compound (8a) and/or its salt (8a'):

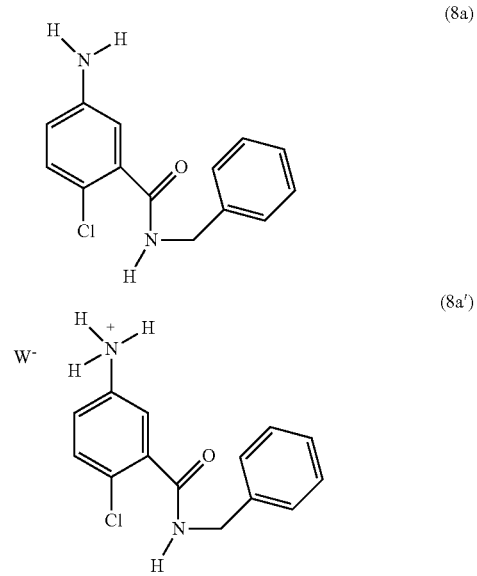

wherein

W⁻ (in the case of compound (8a')) is selected from the group consisting of F⁻, Cl⁻, Br⁻, J⁻, HSO₄⁻, CH₃COO⁻, BF₄⁻, CH₃SO₃⁻, Toluensulphonic acid, CF₃COO⁻ or CF₃SO₃⁻.

Step 8

In Step 8, compounds according to the invention of the type (II), preferably (II'), more preferably (IIa), can be synthesized by reacting amines of the general structure (8) (or their salts) with intermediate (7') which is an activated form of carboxylic acid derivative of formula (7), preferably of formula (7a). The reaction can be carried out with or without solvents. In this step, a suitable base can likewise be used.

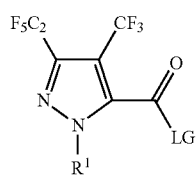

(7')

wherein $R^1$ is hydrogen, optionally halogenated $C_1$-$C_4$-alkyl or optionally halogenated cyclopropyl, preferably methyl.

An activated form of carboxylic acid derivative of formula 7, preferably formula (7a), which is indicated in the reaction scheme of Step 8 above by having any leaving group LG in the —C(=O)LG group, encompasses a) analogs of formula (7) or (7a), respectively, wherein the OH of the COOH group is replaced by a suitable leaving group such as halogen; b) anhydrates of compounds of formula (7) or (7a), respectively; or c) compounds of formula (7) or (7a), respectively in the presence of a coupling reagent which presence activates the compound of formula (7) or (7a), respectively, in the sense of the present invention, such as dicyclohexylcarbodiimide or 1-hydroxybenzotriazole. The skilled person is aware of suitable leaving groups preparation of anhydrates of a carboxylic acid or suitable coupling reagents for acid/amine reactions and the preparation of such compounds. Preferred leaving groups are carboxylic acid halides such as carboxylic acid chlorides or fluorides.

Cyclic carboxylic acid halides, as inter alia represented by the general structure (7'), can be prepared simply by reacting a heterocyclic carboxylic acid of compound (7) with halogenating reagents such as thionyl chloride, thionyl bromide, phosphoryl chloride, oxalyl chloride, phosphorus trichloride, etc. (Houben-Weyl (1952) vol. VIII, p. 463 ff.).

Amines derivatives of the formula (7) and their salts are known in the art, commercially available or can be prepared in a known manner (see, e.g., WO 2010/051926).

The synthesis of carboxamides represented by the formula (II), preferably (II'), more preferably (IIIa), can, however, also be carried out using coupling reagents such as dicyclohexylcarbodiimide and additives such as 1-hydroxybenzotriazole (Konig et al. Chem. Ber. (1970), 788-798). It is also possible to use coupling reagents such as 1-ethyl-3-(3-dimethylaminopropyl)carbodiimide, 1,1'-carbonyl-1H-imidazole and similar compounds.

Coupling reagents which are used for carrying out the synthesis process are all those which are suitable for the preparation of an ester or amide bond (cf. e.g. Bodansky et al., Peptide Synthesis, 2nd ed., Wiley & Sons, New York, 1976; Gross, Meienhofer, The Peptide: Analysis, Synthesis, Biology (Academic Press, New York, 1979).

Furthermore, mixed anhydrides can also be used for the synthesis of (II), preferably (II'), more preferably (IIa) (see, e.g., Anderson et al, J. Am. Chem. Soc (1967), 5012-5017). In this process it is possible to use various chloroformates, such as, for example, isobutyl chloroformate, isopropyl chloroformate. Similarly, diethylacetyl chloride, trimethylacetyl chloride and the like can be used for this.

In general, Step 8 can be carried out optionally/if appropriate, in the presence of a suitable diluent/solvent and, optionally/if appropriate, in the presence of suitable basic reaction auxiliary.

The process according to the invention can be performed in the presence of a diluent/solvent. Useful diluents for this purpose include all inert organic solvents, preferably aliphatic, alicyclic or aromatic hydrocarbons, for example petroleum ether, hexane, heptane, cyclohexane, methylcyclohexane, benzene, toluene, xylene or decalin; halogenated hydrocarbons, for example chlorobenzene, dichlorobenzene, dichloromethane, chloroform, tetrachloromethane, dichloroethane or trichloroethane; ethers such as diethyl ether, diisopropyl ether, methyl t-butyl ether, methyl t-amyl ether, dioxane, tetrahydrofuran, 1,2-dimethoxyethane, 1,2-diethoxyethane or anisole; ketones such as acetone, butanone, methyl isobutyl ketone or cyclohexanone; nitriles such as acetonitrile, propionitrile, n- or i-butyronitrile or benzonitrile; amides such as N,N-dimethylformamide, N,N-dimethylacetamide, N-methylformanilide, N-methylpyrrolidone or hexamethylphosphoramide, more preferably are used chlorobenzene and toluene.

Preferred diluents are aliphatic, alicyclic or aromatic hydrocarbons, for example petroleum ether, hexane, heptane, cyclohexane, methylcyclohexane, benzene, toluene, xylene or decalin; and halogenated hydrocarbons, for example chlorobenzene, dichlorobenzene, dichloromethane, chloroform, tetrachloromethane, dichloroethane or trichloroethane; e.g. toluene or chlorbenzene.

The solvent which may be used is any solvent which does not adversely affect the reaction, such as, for example, water. Of suitability are aromatic hydrocarbons such as benzene or toluene; halogenated hydrocarbons such as dichloromethane, chloroform or tetrachloromethane, open-chain or cyclic ethers such as diethyl ether, dioxane, tetrahydrofuran or 1,2-dimethoxyethane; esters such as ethyl acetate and butyl acetate; ketones such as, for example, acetone, methyl isobutyl ketone and cyclohexanone; amides such as dimethylformamide and dimethylacetamide; nitriles such as acetonitrile; and other inert solvents such as 1,3-dimethyl-2-imidazolidinone; the solvents can be used alone or in combination of two or more.

The base (basic reaction auxiliary) used can be an acid acceptor such as an organic base such as triethylamine, ethyldiisopropylamine, tri-n-butylamine, pyridine and 4-dimethylaminopyridine; furthermore, the following bases can, for example, be used: alkali metal hydroxides, such as, for example, sodium hydroxide and potassium hydroxide; carbonates such as sodium hydrogencarbonate and potassium carbonate; phosphates such as dipotassium hydrogenphosphate and disodium phosphate; alkali metal hydrides, such as sodium hydride; alkali metal alcoholates, such as sodium methanolate and sodium ethanolate. These bases can be used in ratios of from 0.01 to 5.0 mole equivalents based on (8) and (7'). Furthermore, silver(I) cyanide can also be used as base and activator (see, e.g., Journal of Organic Chemistry. 1992, 57, 4394-4400; Journal of Medicina Chemistry 1992, 35, 3905-3918; Journal of Organic Chemistry 2003, 68, 1843-1851).

However, in one preferred embodiment of the present invention, step 8 is carried out in the absence of an acid acceptor and the leaving group is Cl or F, more preferably Cl.

In the context of the invention, "in the absence of an acid acceptor" means in the absence of an acid acceptor other than the amine reactant (8) or, in other words, "in the absence of an additional acid acceptor wherein "additional" means in addition to the amine derivative of the formula (8) (or its salts (8') which is part of the reaction. An "additional acid acceptor" in the sense of the present invention can be a base in addition to the amine compound according to the invention or compounds which reduce the strength of a formed acid such as salts, e.g. silvercyanide (AgCN), which are able to transform strong acids which are formed during the reaction (leaving group anion plus hydrogen cation) into insoluble salts and weak acids (e.g. formed HCl (if the leaving group is chlorine) reacts with AgCN to insoluble AgCl and weak base HCN).

Surprisingly, the carboxamides of the formula (II) can be prepared in the absence of an acid acceptor with good yields in high purity and selectivity. A further advantage of the process according to the invention is that the workup is simpler, since an acid acceptor is not needed. This causes fewer or no waste water, an easier purification process without prior isolation by addition of an aliphatic alcohol in the same reaction vessel, and the process can be run in a higher concentration. The resulting product has then been obtained with a surprising purity superior to 90% or even close to 100%, and with less reagent and effort, while prior conditions in presence of an acid acceptor generally leads to a purity close to less than 90% The process according to the invention becomes more economically viable.

Thus, one preferred embodiment refers to a reaction for the production of compounds of formula (IIa)

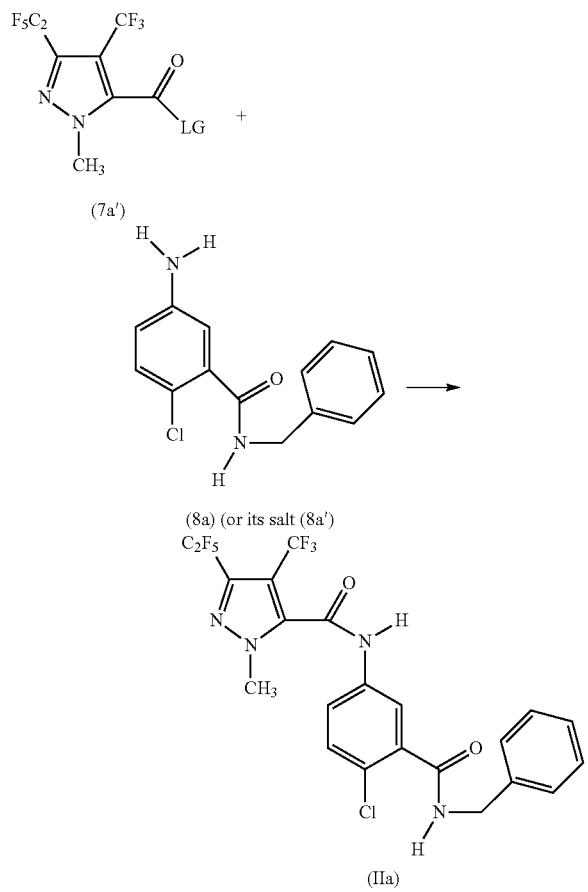

wherein leaving group LG refers to F, Cl, Br or I, preferably F or Cl, and in the absence of an acid acceptor in addition to compound (8a).

The suitable reaction temperature is in the range from −20° C. up to the boiling point of the particular solvent. In general, the reaction temperature is between 70° C. to 150° C., preferably between 80° C. to 140° C., e.g. 100° C. or around 100° C. such as 80° C. to 130° C. or 80° C. to 120° C.

The reaction time is between 1 min and 96 h depending on the choice of volume, reactants, solvents and reaction temperature.

For the process of Step 8, generally between 0.8 and 1.5 mol, preferably 0.8 to 1.4 mol, 0.9 to 1.4 mol, equimolar amounts or 1 to 1.2 mol of amine derivative of the formula (8) or its salt, preferably (8a) or (8a'), are used per mole of the pyrazole-carboxamide derivatives (7').

One preferred embodiment refers to a reaction of a compound (8a) or its salt (8a'), respectively, with compound (7'), wherein X is Cl and wherein the ratio of compound (8a) (or its salt (8a')) and (7') wherein X is Cl is between 1:1 or 1:1.3, preferably between 1:1 to 1:2 such as between 1:1 to 1:1 or even 1:1.

Depending on the choice of volume, reactants, solvents and reaction temperature, the reaction time can vary between one minute and 96 h. Typically, the reaction time is up to 15 hours, but the reaction can also be terminated even earlier in the case of complete conversion. Preference is given to reaction times of 5-10 hours.

The reaction of Step 8 is generally performed under standard pressure. However, it is possible to work under elevated or reduced pressure—generally between 0.1 bar and 10 bar It is preferable to work under reduced pressure to remove HCl from the reaction volume.

The reaction of Step 8 can generally be performed under atmosphere. However, it is preferred to carry out the process under protective gas such as argon. or nitrogen.

Moreover the skilled person will understand that it is also possible to react a compound of formula (7') with a compound of formula (8*), wherein the —C(=O)—NH—Q moiety of compounds of formula (8) is replaced by a C(=O)—OH or C(=O)—PG moiety in a compound of formula (8*), wherein PG stands for any protective group of a carboxylic group (e.g. a methylester, i.e. PG represents —O-methyl). The deprotection of the carboxylic moiety of the resulting compound (II*) of a reaction with a compound (8*) and/or activating of the carboxylic moiety and/coupling with an amine to arrive at a compound of formula (II) are well known to a skilled person. Compounds of the general structure (II*) can be synthesized by reacting an amine of the general structure (7) with activated carboxylic acid derivatives of the general structure (8*). In this connection, the same conditions apply for the choice of solvent, the reaction conditions, the reaction time and the reagents as for the synthesis of (II), described above.

Step 7

Compounds of the general structure (8) can be synthesized by reacting an amine of the general structure (10) with activated carboxylic acid derivatives of the general structure (9). In this connection, the same conditions apply for the choice of solvent, the reaction conditions, the reaction time and the reagents as for the synthesis of (II), preferably (II'), more preferably (IIa), described in step 8 above.

Compounds of Formula (III)

The present invention also refers to a process to produce an insecticidal compound of formula (III) or (III') based on the preparation of compounds of formula (I).

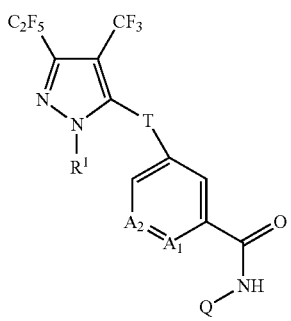

(III)

in which
R¹ is (C₁-C₄)-alkyl, preferably methyl; and
A₁ is C—R²;
R² is hydrogen, fluorine, chlorine, bromine, CN, NO₂, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl or N-cyclopropylaminocarbonyl (—C(=O)—NH—cyclopropyl); preferably hydrogen, fluorine, chlorine, bromine, CN, NO₂, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, NO₂, methyl, fluoromethyl, difluoromethyl, trifluoromethyl, 2,2,2-trifluoroethyl, methoxy, ethoxy, or pentafluoroethoxy, preferably hydrogen, fluorine, chlorine, bromine, most preferably chlorine; and
A₂ is C—R³ or nitrogen;
R³ is hydrogen, methyl, fluorine or chlorine, preferably hydrogen; and
Q is hydrogen, cyano, hydroxy, formyl or one of the groupings $C_1$-$C_6$-alkyl, $C_3$-$C_6$-alkenyl, $C_3$-$C_6$-alkynyl, $C_3$-$C_9$-cycloalkyl, $C_3$-$C_9$-heterocycloalkyl, $C_1$-$C_4$-alkoxy, $C_4$-$C_{15}$-alkylcycloalkyl, $C_4$-$C_{15}$-cycloalkylalkyl, $C_1$-$C_6$-hydroxyalkyl, $C_6$-aryl-$C_1$-$C_3$-alkyl, $C_5$-$C_6$-heteroaryl-$C_1$-$C_3$-alkyl, $C_1$-$C_4$-aminoalkyl, aminocarbonyl-$C_1$-$C_4$-alkyl or $C_1$-$C_4$-alkyl-amino-$C_1$-$C_4$-alkyl which are optionally substituted with one, two, three, four or five, preferably with one or two, more preferably with one, substituents independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and optionally independently with one, two or three substituents selected from the group consisting of halogen, cyano, nitro, hydroxycarbonyl, $C_1$-$C_2$-alkylcarbamoyl, $C_1$-$C_2$-alkyl, halogenated $C_1$-$C_2$-alkyl and $C_1$-$C_2$-alkoxy substituted phenyl; preferably Q is $C_3$-$C_6$-cycloalkyl, or $C_3$-$C_6$-cycloalkyl which is substituted with at least one substituent selected from the group consisting of chlorine, fluorine, bromine, iodine, cyano and hydroxy, or $C_6$-aryl-$C_1$-$C_3$-alkyl; more preferably cyclopropyl, 1-cyano-cyclopropyl or benzyl (—CH₂—C₆H₅);
T represents one of the 5-membered heteroaromatics T1-T8 listed below, where the bond to the pyrazole head group is marked with an asterisk *,

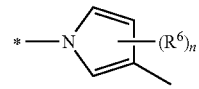 T1

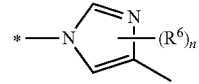 T2

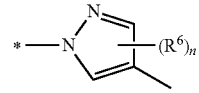 T3

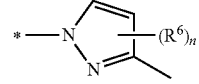 T4

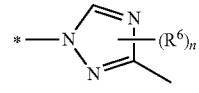 T5

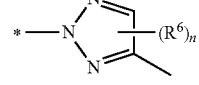 T6

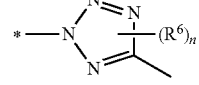 T7

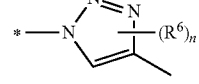 T8 wherein
R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n represents the values 0-2, preferably 0, provided that n is 0 or 1 in T5, T6 and T8 and provided n is 0 in T7;
preferably, a compound of formula (III) is a compound of formula (III')

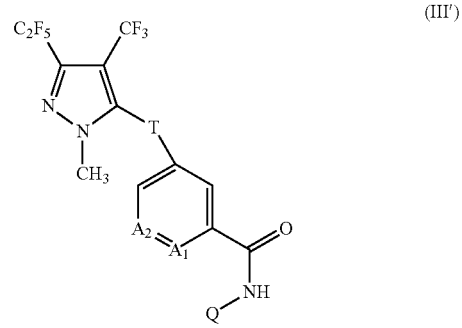

(III')

wherein A₁ and A₂ and T and Q have the meanings described above for a compound of formula (II) characterized in that the process comprises steps 3 and 4 as described above.

For clarity sake, if n in any formula described herein is 0 (zero), carbon ring atoms with a free valence are then substituted by hydrogen.

In one preferred embodiment, the compound of formula (III) is compound (IIIa) defined by the following substituents:

| $R^1$ | T | n | $R^6$ | $A^1$ | $A^2$ | Q |
|---|---|---|---|---|---|---|
| $CH_3$ | T3 | 0 | — | C—Cl | C—H | 1-cyanocyclopropyl 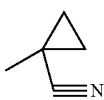 |

The new and inventive process for preparing a compound of formula (III), preferably (III'), more preferably (IIIa), is characterized in that the process comprises steps 3 and 4 as described above. In one preferred embodiment, the process is characterized in that it comprises steps 1 to 4 described above. In a further preferred embodiment, the process comprises in addition to steps 3 and 4 or in addition to steps 1 to 4 the subsequent Step 9 and Step 10:

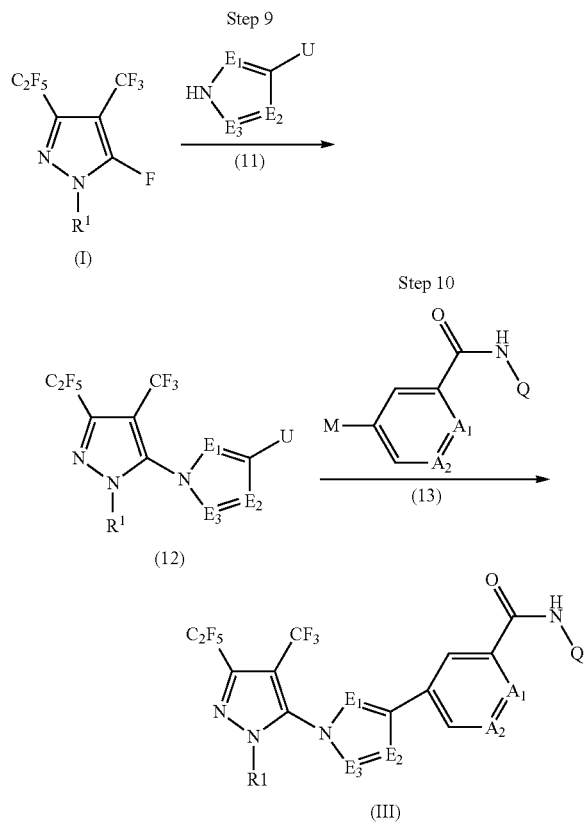

The radicals $A_1$, $A_2$, $R^1$ and Q have the meanings described for compound (III). Preferably, $R^1$ is methyl. The five-membered cycles of $E_1$-$E_3$, carbon and nitrogen represent the 5-membered heterocycles defined under T. U represents bromine, iodine or triflate if M represents a boronic acid, boronic ester or trifluoroboronate. U represents a boronic acid, boronic ester or trifluoroboronate if M represents bromine, iodine or triflate.

Step 9

The compounds of the general structure (12) can be prepared by processes known from the literature by, e.g., nucleophilic substitution of F at the aromatic ring (WO2007-107470; Sakya et al., Tetrahedron Letters 2003, 44, 7629-7632) from the appropriate starting materials (I), preferably (Ia), and (11).

Step 10

Compounds of formula (III) or (III'), preferably compound (Ia), can be prepared by using palladium-catalysed reactions with the reaction partners (12) and (13) (see, e.g., WO 2005/040110 or WO 2009/089508). The compounds of the general structure (13) are either commercially available or can be prepared by processes known to the person skilled in the art.

Moreover, the skilled person is aware that it is alternatively possible to react a compound of formula (12) with a compound of formula (13*), wherein the —C(=O)—NH—Q moiety of compounds of formula (13) is replaced by a C(=O)—OH or C(=O)—PG moiety in a compound of formula (13*), wherein PG stands for any protective group of a carboxylic group (e.g. an alkylester such as methylester, i.e. PG represents —O— methyl). The deprotection of the carboxylic moiety of the resulting compound (III*) of a reaction with a compound (13*) and/or activating of the carboxylic moiety and/coupling with an amine to arrive at a compound of formula (III) are well known to a skilled person.

In sum, compounds of the general structure (III) can be synthesized by reacting an amine of the general structure (10) with activated carboxylic acid derivatives of the general structure (III*). In this connection, the same conditions apply for the choice of solvent, the reaction conditions, the reaction time and the reagents as for the synthesis of (II), described in step 8 above.

Compounds of formula (III")

In another preferred embodiment, the invention refers to a process to prepare a compound of formula (III"), preferably of formula (II"'), e.g., known from WO 2012/107434:

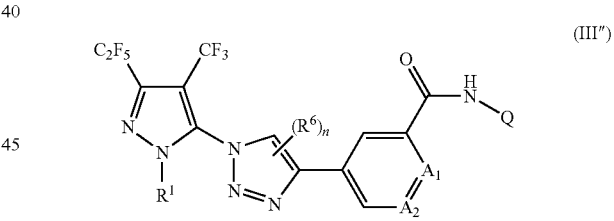

wherein $R^1$, $R^6$, n, $A_1$, $A_2$, and Q are as defined for compound (II), preferably;
preferably, a compound of formula (III") is a compound of formula (III''')

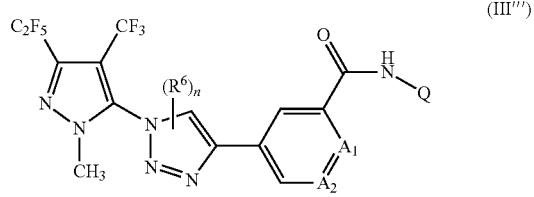

wherein $R^6$, n, $A_1$, $A_2$ and Q are as defined for a compound of formula (III), preferably, wherein n is 0 characterized in that the process comprises steps 3 and 4 as described above.

In one preferred embodiment, the compound of formula (III''') is compound (IIIb) defined by the following substituents:

| n | R⁶ | A¹ | A² | Q |
|---|----|----|----|---|
| 0 | — | C—Cl | C—H | 1-cyanocyclopropyl |

The process for preparing a compound of formula (III''), preferably (III'''), more preferably (IIIb), is characterized in that the process comprises steps 3 and 4 as described above. In one preferred embodiment, the process is characterized in that it comprises steps 1 to 4 described above. In a further preferred embodiment, the process comprises in addition to steps 3 and 4 or in addition to steps 1 to 4 optionally the subsequent Step 9 and Step 10 as described above or optionally the subsequent Step 11 and Step 12. Steps 11 and 12 are known in the art (see, e.g., WO 2012/107434).

Step 11

In a step 11, a compound of formula (I), preferably of formula (Ia), can be transformed into its azido analogue of formula (14) or (14a), respectively:

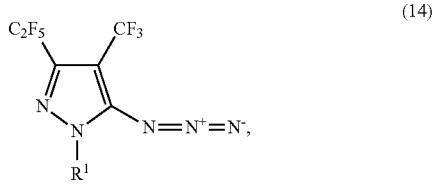

wherein R¹ is hydrogen, optionally halogenated $C_1$-$C_4$-alkyl or optionally halogenated cyclopropyl, preferably methyl, preferably, a compound of formula (14) is compound (14a)

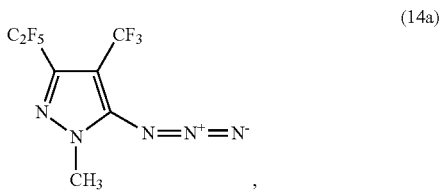

by reacting compound (I), preferably compound (Ia), with an azide-donor such an alkaline metal azide (e.g., NaN₃).

Preferably, the reaction is carried out in a polar aprotic solvent such as tetrahydrofuran (THF), ethyl acetate (EtOAc), acetone, dimethylformamide (DMF), acetobitrile or dimethyl sulfoxide (DMSO). One preferred solvent is DMSO.

Typically, the reaction temperature is between 0° C. and 60° C., preferably between 10° C. and 30° C., more preferably between 20° C. and 30° C.

The reaction time can inter alia depend on the reaction volume and is usually between 0.5 h to 30 h.

Step 12

In a step 12, an intermediate of formula (14), preferably of formula (14a), is reacted with an intermediate of formula (15) to give an intermediate of formula (III''*) or preferably a compound of formula (III'''*) wherein $R^1$ is methyl, respectively:

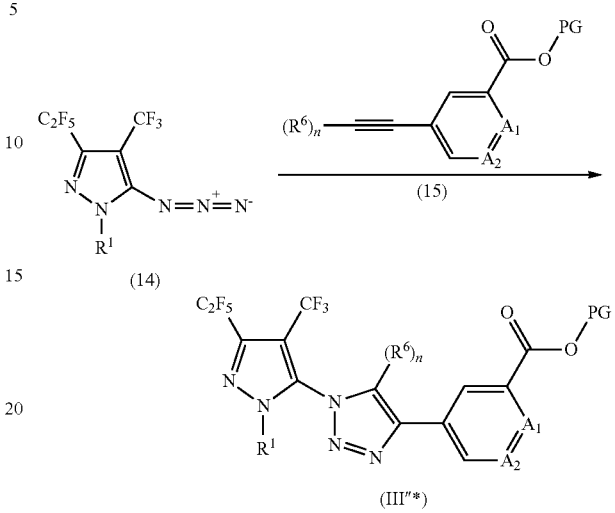

wherein $R^1$, $R^6$, $A_1$, and $A_2$ are as defined for compound (III), n is 0 or 1 and PG is any protective group of the carboxylic group such as $C_1$-$C_6$-alkyl (e.g., methyl). Preferably, $R^1$ in a compound of formula (III''*) is methyl (compound of formula (III'''*)). More preferably, $R^1$ in formula (III''*) is methyl and n in formula (III''*) is 0.

Compounds of formula (15) are commercially available or can be prepared according to methods known in the art.

Typically, the solvent for reaction of Step 12 is a polar protic solvent such as water, formic, n-butanol, isopropanol, nitromethane, ethanol, methanol, acetic acid or combinations thereof. Preferably, the solvent is n-butanol, isopropanol, ethanol, water or combinations thereof.

The reaction is carried out in the presence of copper or a copper catalyst such as copper sulfate or copper (1) iodide, optionally in the presence of a base such as N-ethyldiisopropylamine. However, also other organic bases are suitable. In case of a Cu(II) catalyst, a reducing agent such as sodium ascorbate may be used. In case of Cu(0) catalyst, such as an amine salt, an oxidizing agent may be used (see, e.g., Angewandte Chemie, International Edition (2009), 48(27), 4900-4908 and cited references, Lutz., Angew. Chem. Int. Ed. 2008, 47, 2182-2184 and cited references, and Bock et al., Eur. J. Org. Chem. (2006), 51-68 and cited references).

Starting from a compound of formula (III''*), compounds of formula (III), (III'), (III''), (III'''), (IIIb), (III''''), (IV) or (IV') can be easily prepared according to methods known in the art (see, e.g. WO 2012/107434).

Step 13

Compound of formula (III'''') may be prepared by reaction of a compound of formula (III''*) wherein O-PG is $C_1$-$C_6$-alkoxy via hydrolysis. For instance, in the case wherein —O-PG is methoxy or ethoxy, the hydrolysis can be done with water and a base, such as potassium hydroxide or lithium hydroxide, in the absence or in the presence of a solvent, such as, for instance, tetrahydrofurane or methanol. In the case where R is, for example, tert-butoxy, the hydrolysis is done in the presence of acid, such as trifluoroacetic acid or hydrochloric acid. The reaction is carried out at a temperature of from −120° C. to 130° C., preferably from −100° C. to 100° C.

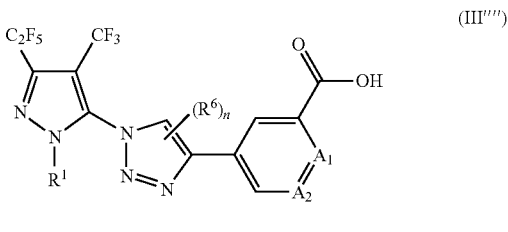
(III'''')

wherein $R^1$, $R^6$, n, $A_1$, and $A_2$ are as defined for compound (III), preferably $R^1$ is methyl and n is 0.

Compounds of the general structure (III) can be synthesized by reacting an amine of the general structure (10) with activated carboxylic acid derivatives of the general structure (III''''). In this connection, the same conditions apply for the choice of solvent, the reaction conditions, the reaction time and the reagents as for the synthesis of (II) described in step 8 above.

Compounds of Formula (IV)

One aspect of the present invention refers to a process for the preparation of a compound of formula (IV), preferably of formula (IV'):

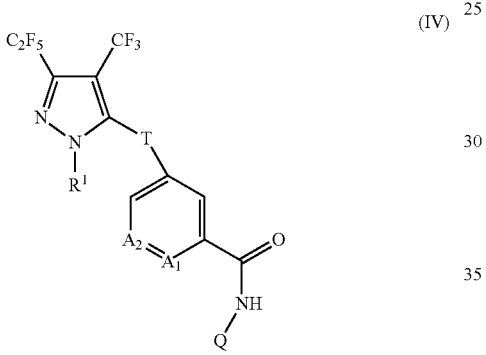
(IV)

in which
$R^1$ is $C_1$-$C_4$-alkyl, preferably methyl; and
$A_1$ is C—$R^2$; and
$R^2$ is hydrogen, fluorine, chlorine, bromine, CN, $NO_2$, optionally halogenated $C_1$-$C_6$-alkyl, optionally halogenated $C_1$-$C_4$-alkoxy, optionally halogenated $C_1$-$C_4$-alkylsulphonyl, optionally halogenated $C_1$-$C_4$-alkylsulphinyl or N-cyclopropylaminocarbonyl (—C(=O)—NH—cyclopropyl); preferably hydrogen, fluorine, chlorine, bromine, CN, $NO_2$, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, $NO_2$, methyl, fluoromethyl, difluoromethyl, trifluoromethyl, 2,2,2-trifluoroethyl, methoxy, ethoxy, or pentafluoroethoxy, preferably hydrogen, fluorine, chlorine, bromine, most preferably chlorine; and
$A_2$ is C—$R^3$ or nitrogen; and
$R^3$ is hydrogen, methyl, fluorine or chlorine, preferably hydrogen; and
T represents one of the 5-membered heteroaromatics T1-T9 listed below, where the bond to the pyrazole head group is marked with an asterisk *,

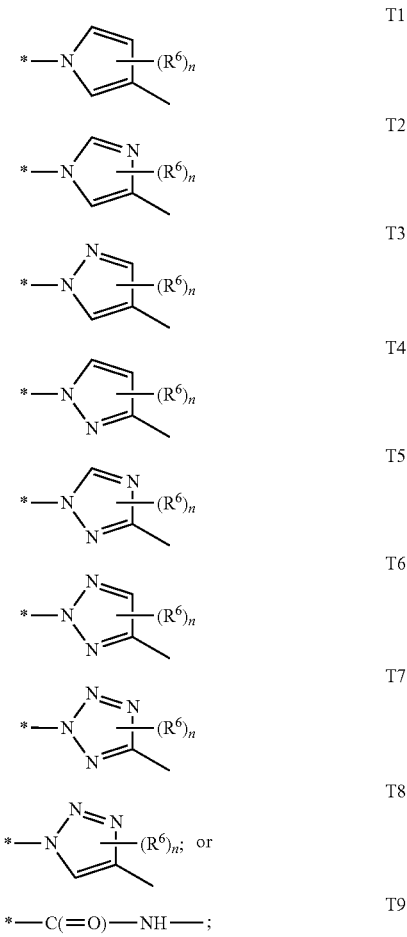

and
$R^6$ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, preferably 0, provided that n is 0 or 1 in T5, T6 and T8 and provided n is 0 in T7.
Q is hydrogen, cyano, hydroxy, formyl or one of the groupings $C_1$-$C_6$-alkyl, $C_3$-$C_6$-alkenyl, $C_3$-$C_6$-alkynyl, $C_3$-$C_9$-cycloalkyl, $C_3$-$C_9$-heterocycloalkyl, $C_1$-$C_4$-alkoxy, $C_4$-$C_{15}$-alkylcycloalkyl, $C_4$-$C_{15}$-cycloalkylalkyl, $C_1$-$C_6$-hydroxyalkyl, $C_6$-aryl-$C_1$-$C_3$-alkyl, $C_5$-$C_6$-heteroaryl-$C_1$-$C_3$-alkyl, $C_1$-$C_4$-aminoalkyl, aminocarbonyl-$C_1$-$C_4$-alkyl or $C_1$-$C_4$-alkyl-amino-$C_1$-$C_4$-alkyl which are optionally substituted with one, two, three, four or five, preferably with one or two, more preferably with one, substituents independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and optionally independently with one, two or three substituents selected from the group consisting of halogen, cyano, nitro, hydroxycarbonyl, $C_1$-$C_2$-alkylcarbamoyl, $C_1$-$C_2$-alkyl, halogenated $C_1$-$C_2$-alkyl and $C_1$-$C_2$-alkoxy substituted phenyl; preferably Q is $C_3$-$C_6$-cycloalkyl, or $C_3$-$C_6$-cycloalkyl which is substituted with at least one substituent selected from the group consisting of chlorine, fluorine, bromine, iodine, cyano and hydroxy, or $C_6$-aryl-$C_1$-$C_3$-alkyl; more preferably cyclopropyl, 1-cyano-cyclopropyl or benzyl (—$CH_2$—$C_6H_5$);

preferably, a compound of formula (IV) is a compound of formula (IV'):

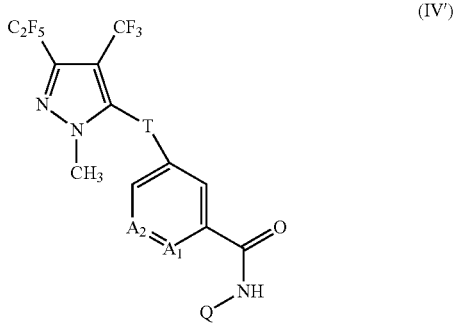

wherein T, $A_1$, $A_2$ and Q are as defined for a compound of formula (IV), preferably wherein T is selected from T3, T8 or T9 wherein the process is characterized in that the process comprises steps 3 and 4 as described above. In one preferred embodiment, the process is characterized in that it comprises steps 1 to 4 described above.

One preferred embodiment refers to a process for the preparation of compound (IV) where $R^1$—in all formulae disclosed herein wherein $R^1$ is present—represents methyl.

Another preferred embodiment refers to a process for the preparation of compound (IV) where n—in all formulae disclosed herein wherein n is present—represents 0.

Another preferred embodiment refers to a process for the preparation of compound (IV) where $A_1$—in all formulae disclosed herein wherein $A_1$ is present—represents C—$R^2$, wherein $R^2$ represents hydrogen, fluorine, chlorine or bromine, most preferably wherein $R^2$ represents chlorine.

Another preferred embodiment refers to a process for the preparation of compound (IV) where $A_2$—in all formulae disclosed herein wherein $A_2$ is present—represents C—$R^3$ wherein $R^3$ represents hydrogen.

Another preferred embodiment refers to a process for the preparation of compound (IV) where T—in formula (IV) and all further formulae disclosed herein wherein T is present—represents T3, T8 or T9.

Another preferred embodiment refers to a process for the preparation of compound IV where Q—in all formulae disclosed herein wherein Q is present—represents optionally with cyano substituted $C_3$-$C_6$-cycloalkyl or $C_6$-aryl-$C_1$-$C_3$-alkyl even more preferred Q represents optionally with cyano substituted $C_3$-cycloalkyl or benzyl, even more preferred, Q represents with cyano substituted cyclopropyl (e.g., 1-cyano-cyclopropyl) or benzyl.

Another preferred embodiment refers to a process for the preparation of compound (IV) where $R^1$—in all formulae disclosed herein wherein $R^1$ is present—represents methyl and n—in all formulae disclosed herein wherein n is present—represents 0 and $A_1$—in all formulae disclosed herein wherein $A_1$ is present—represents C—Cl and $A_2$—in all formulae disclosed herein wherein $A_2$ is present—represents C—H and where T—in formula (IV) and all further formulae disclosed herein wherein T is present—represents T3, T8 or T9, and Q in all formulae disclosed herein wherein Q is present represents optionally with cyano substituted $C_3$-$C_6$-cycloalkyl or $C_6$-aryl-$C_1$-$C_3$-alkyl.

Another preferred embodiment refers to a process for the preparation of compound IV where $R^1$—in all formulae disclosed herein wherein $R^1$ is present—represents methyl and T—in all formulae disclosed herein wherein T is present—represents T3, T8 or T9 and n—in all formulae disclosed herein wherein n is present—represents 0 and $A_1$—in all formulae disclosed herein wherein $A_1$ is present—represents C—Cl and $A_2$—in all formulae disclosed herein wherein $A_2$ is present—represents C—H and Q—in all formulae disclosed herein wherein Q is present—represents with cyano substituted cyclopropyl (e.g. 1-cyano-cyclopropyl) or benzyl.

The present invention also refers to a process for the preparation of a compound of formula (6), preferably of formula (6a), comprising the steps 3 and 4 as described above. In one preferred embodiment, the process is characterized in that it comprises steps 1 to 4 described above.

The present invention also refers to a process for the preparation of a compound of formula (6), preferably of formula (6a), comprising the steps 3 and 4 as described above. Or comprising the steps 1 to 4 described above and step 5 as described above.

The present invention also refers to a process for the preparation of a compound of formula (7), preferably of formula (7a), comprising the steps 3 and 4 as described above. In one preferred embodiment, the process is characterized in that it comprises steps 1 to 4 described above.

The present invention also refers to a process for the preparation of a compound of formula (7), preferably of formula (7a), comprising the steps 3 and 4 as described above or comprising the steps 1 to 4 described above and steps 5 and 6 as described above.

The present invention also refers to a process for the preparation of a compound (I), (II), (II) or (IV), wherein Step 3 and Step 4 are carried out in the same solvent, preferably acetonitrile or methylene chloride, more preferably methylene chloride.

The present invention also refers to a process for the preparation of a compound (I), (II), (III) or (IV), wherein Step 3 and Step 4 are carried out as a one-pot reaction in the same solvent, preferably acetonitrile or methylene chloride, more preferably methylene chloride.

The present invention also refers to a process for the preparation of a compound (I), (II), (111) or (IV), wherein Step 2, Step 3 and Step 4 are carried out in the same solvent.

The present invention also refers to a process for the preparation of a compound (I), (I), (III) or (IV), wherein Step 2, Step 3 and Step 4 are carried out as a one-pot reaction in the same solvent.

In one aspect, the present invention also refers to the use of compounds of formula (1) prepared by a process comprising at least steps 3 and 4 as described herein to prepare a compound of formula (II), preferably of formula (IIa).

Moreover, the present invention also refers to the use of compounds of formula (1) prepared by a process comprising at least steps 3 and 4 as described herein to prepare a compound of formula (III), preferably of formula (III'), more preferably of formula (IIIa).

Moreover, the present invention also refers to the use of compounds of formula (1) prepared by a process comprising at least steps 3 and 4 as described herein to prepare a compound of formula (III"), preferably of formula (III'"), more preferably of formula (IIIb).

Moreover, the present invention also refers to the use of compounds of formula (1) prepared by a process comprising at least steps 3 and 4 as described herein to prepare a compound of formula (IV), preferably of formula (IV').

Example 1 (Step 1)

Preparation of Perfluoro-2-methyl-4-pentene (Intermediate (2))

Into a suspension of 5 g CsF in 100 ml acetonitrile (CH$_3$CN) 300 g of hexafluoropropen (HFP) were slowly introduced to keep the temperature in reactor below 30° C. After introduction of HFP the mixture was heated for 8 h at 50-55° C. and cooled to 10° C. The bottom layer was separated and distilled at yielding 260 g of Perfluoro-2-methyl-4-pentene. Yield 87%. B.p. 50° C.

Example 2 (Step 2)

Preparation of Perfluoro-2-methyl-2-pentene (Intermediate (3))

Perfluoro-2-methyl-4-pentene 210 g and 1 g of dry CsF in 300 ml CH$_3$CN were heated for 8 h at 50-55° C. The mixture was cooled to 5-10° C. and phases were separated. The bottom phase 195 g (93%) (pure perfluoro-2-methyl-2-pentene) was used without purification for the preparation of perfluoro-2-methyl-2-penten-)-3-triethylammonium-enolate according to example 3.

Example 3 (Step 3)

Preparation of 5-Fluoro-3-pentafluoroethyl-4-trifluoromethyl-1H-pyrazol (Intermediate (4))

A solution of 15 g (50 mmol) of perfluoro-2-methyl-2-pentene and 10.1 g of triethylamine in 40 ml acetonitrile were mixed together and stirred for 30 min. 5.1 g (50 mmol) of propionylhydrazine was added at 0° C. to the mixture and the mixture was heated for 4 h at 40° C. 100 ml water was added to the reaction mixture and product was extracted with methylene chloride. The extract was washed with water and evaporated.

The residue was distilled under reduced pressure. B.p. 60-61° C./1 mbar. Yield 9.5 g.

$^1$H-NMR (400 MHz, d$_3$-acetonitrile): δ=8.2 ppm.
$^{19}$F-NMR (400 MHz, CDCl$_3$): δ=−56.3 (3F), −85.9 (3F), −113.9 (2F), 128.8 (F) ppm.

[1] The stated mass is the peak of the isotope pattern of the [M+H]$^+$ ion with the highest intensity.

Example 4 (Step 4)

Preparation of N-methyl-3-pentatfluoroethyl-4-trifluoromethyl-5-fluorpyrazol (Compound (Ia))

27.2 g (0.1 mol) of 3-pentafluoroethyl-4-trifluoromethyl-5-fluorpyrazol, 27.6 g of Potassium carbonate and 28 g methyliodid in 200 ml DMF were stirred at RT for 3 h. GC shows that 78% of the diesred product together with 22% of isomer. The mixture was diluted with water, the product extracted with Ethylacetate and organic extract washed with water and dried over MgSO$_4$. The solvent was removed in in vacuo 300 mbar to give an oil. The mixture was distilled in vacuo to give pure isomer with boiling point 50-55° C./10 mbar.

$^{19}$F NMR δ: 53.7 (3F), 83.9 (3F), 112.1 (2F), 125.1 (1F) ppm.
Yield 20.3 g 71%,

Example 5 (Step 5)

Preparation of 5-Cyano-1-methyl-3-pentafluoroethyl-4-trifluoromethyl-1H-pyrazole (Intermediate (6a))

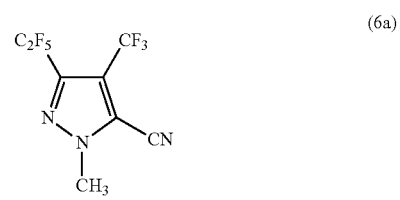

(6a)

28.6 g (0.1 mol) of 5-fluoro-1-methyl-3-pentafluoroethyl-4-trifluoromethylpyrazole (compound (Ia)) and 9.7 g (0.15 mol) of potassium cyanide are suspended in 150 ml of acetonitrile and then heated under reflux for 5 h under a protective gas atmosphere. After cooling, the precipitate (KCN, KF) was filtered off, and the solvent was removed in vacuo 300 mbar to give a brawn oil (27.8 g, 95%) which was used for further step without any purification.

$^1$H-NMR (400 MHz, d$_3$-acetonitrile): δ=4.11 (s, 3H, CH$_3$) ppm
$^{19}$F-NMR (400 MHz, CDCl$_3$): δ=−56.7 (3F), −111.4 (3F), −111.6 (2F) ppm.
GC-MS: Retention time 2.67 min; mass (m/z): 224 (M)+.

Example 6 (Step 6)

Preparation of 1-Methyl-3-pentafluoroethyl-4-trifluoromethyl-1H-pyrazole-5-carboxylic acid (Intermediate (7a))

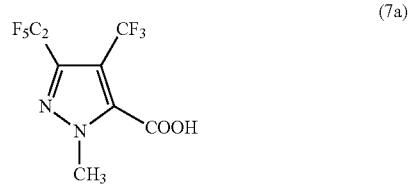

(7a)

29.3 g (0.1 M) of 5-cyano-1-methyl-3-pentafluoroethyl-4-trifluoromethylpyrazole (compound (6a)) and 110 g of 10% NaOH were heated in an oil bath at 100° C. for 6 h until clear solution formed. After cooling to 5° C., the reaction mixture was slowly acidify to pH 1 by adding of 37% HCl to give a white crystals which were filtered off, washed with 40 ml cold water and dried yielding 28 g (7a) of 1-methyl-3-pentafluoroethyl-4-trifluoromethylpyrazole-5-carboxylic acid) as a white solid with m.p. 120-122° C.

$^1$H-NMR (400 MHz, d$_3$-acetonitrile) 5=4.08 (s, 3H, CH$_3$) ppm;
HPLC-MS$^{a)}$: log P=1.86; mass (m/z): 313.0 (M+H)$^+$.

$^{a)}$ Note regarding the determination of the log P values and mass detection: The log P values given were determined in accordance with EEC Directive 79/831 Annex V.A8 by HPLC (High Performance Liquid Chromatography) on a phase inversion column (C18). Agilent 1100 LC system; 50*4.6 Zorbax Eclipse Plus C18 1.8 micron; eluent A: acetonitrile (0.1% formic acid); eluent B: water (0.09% formic acid); linear gradient from 10% acetonitrile to 95% acetonitrile in 4.25 min, then 95% acetonitrile for a further 1.25 min; oven temperature 55° C.; flow: 2.0 ml/min. The mass detection is carried out via an Agilend MSD system.

Example 7 (Step 9)

Preparation of 4-bromo-2'-methyl-5'-(pentafluoroethyl)-4'-(trifluoromethyl)-2'H-1,3'-bipyrazole (Intermediate (12))

2.00 g (6.99 mmol) of 5-fluoro-1-methyl-3-(pentafluoroethyl)-4-(trifluoromethyl)-1H-pyrazole (compound (Ia)), 1.03 g (6.99 mmol) of 4-bromo-1H-pyrazole (compound of formula (11)) and 1.93 g of potassium carbonate are suspended in 50 ml of tetrahydrofuran p.a. The reaction mixture is heated under reflux for 16 h. The cooled reaction mixture is filtered and the solvent is removed under reduced pressure. The residue is purified by column chromatography on silica gel.

This gives 0.69 g of 4-bromo-2'-methyl-5'-(pentafluoroethyl)-4'-(trifluoromethyl)-2'H-1,3'-bipyrazole as a colourless solid.

$^1$H-NMR (400 MHz, d$_3$-acetonitrile): δ=8.00 (s, 1H), 7.91 (s, 1H), 3.71 (s, 3H).

HPLC-MS$^{a)}$: log P=4.14, mass (m/z)=413 [M+H]$^+$.

Example 8 (Step 10)

Preparation of 2-Chloro-N-1-cyano-cyclopropyl-5-[2'-methyl-5'-(pentafluoroethyl)-4'-(trifuoromethyl)-2'H-1,3'-bipyrazol-4-yl]benzamide (Compound (IIIa))

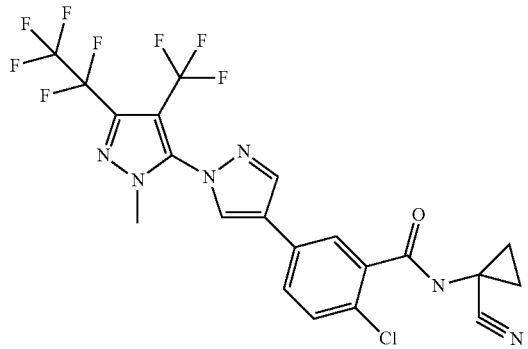

(IIIa)

150 mg (0.36 mmol) 4-bromo-2'-methyl-5'-(pentafluoroethyl)-4'-(trifluoromethyl)-2'H-1,3'-bipyrazole, 126 mg (0.36 mmol) 2-chloro-N-(1-cyanocyclopropyl)-5-(4,4,5,5-tetramethyl-1,3,2-dioxaborolane-2-yl)benzamide, 21 mg (0.01 mmol) tetrakis(triphenylphosphin)palladium and 1.1 ml of 1M aqueous sodium bicarbonate were mixed with 10.5 ml isopropanol and heated under reflux for 3 h. The solvent is removed under reduced pressure and the residue is dissolved in ethylacetat. The organic phase was washed two times with water, dried over Na$_2$SO$_4$, and filtered. The solvent is removed under reduced pressure. The residue was purified vie column chromatography with silica gel, yielding 98 mg 2-chloro-N-(1-cyanocyclopropyl)-5-[2'-methyl-5'-(pentafluoroethyl)-4'-(trifluoromethyl)-2'H-1,3'-bipyrazole-4-yl]benzamide as colorless solid.

$^1$H-NMR (400 MHz, d$_3$-Acetonitril): δ=$^1$H-NMR (400 MHz, d3-Acetonitril): δ=8.27 (s, 1H), 8.25 (s, 1H), 7.75 (d, 1H), 7.70 (dd, 1H), 7.62 (s, 1H), 7.51 (d, 1H), 3.75 (s, 3H), 1.56-1.60 (m, 2H), 1.33-1.36 (m, 2H).

HPLC-MS$^{a)}$: log P=3.72, Masse (m/z)=553.1 [M+H]$^+$.

Example 9 (Step 11)

Preparation of 5-Azido-1-methyl-3-pentafluoroethyl-4-trifluoromethyl-1H-pyrazole (Intermediate (14), R$^1$=Methyl)

5-Fluoro-1-methyl-3-pentafluoroethyl-4-trifluoromethyl-1H-pyrazole (prepared according to steps 1 to 4; 7 mmol) is added to a mixture of dimethyl sulfoxide (DMSO) (10 ml). Sodium azide (0.5 g; 7.7 mmol) is then added into the mixture, which is kept at room temperature. The mixture is stirred overnight at RT. After the reaction is complete, a mixture of water (100 mL) and diethyl ether (100 mL) is added. The phases are separated and the aqueous phase extracted twice with diethyl ether. This compound is used without extra purification.

Example 10 (Step 12)

Preparation of 2-Chloro-5-[1-(2-methyl-5-pentafluoroethyl-4-trifluoromethyl-2H-pyrazol-3-yl)-1H[1,2,3]triazol-4-yl]-benzoic acid methyl ester (see intermediate (III"*))

2-Chloro-5-ethynyl-benzoic acid methyl ester (1.13 g, 5.8 mmol) and 5-Azido-1-methyl-3-pentafluoroethyl-4-trifluoromethyl-1H-pyrazole (1.80 g, 5.8 mmol) is suspended in a mixture of water and t-BuOH (30 ml). Sodium ascorbate (0.600 ml 1 M sol. in water, freshly prepared) is added to the mixture followed by copper (II) sulfate pentahydrate (0.015 g). The resulting heterogeneous mixture is stirred vigorously for 96 hours. The reaction mixture is diluted with water and the product extracted with ethyl acetate. The organic phase is washed with brine, dried over magnesium sulphate and evaporated. The reissue is subjected to silica gel column chromatography (c-HEX/EtOAc=3:1) affording the desired product 2-Chloro-5-[1-(2-methyl-5-pentafluoroethyl-4-trifluoromethyl-2H-pyrazol-3-yl)-1H-[1,2,3]triazol-4-yl]-benzoic acid methyl ester (yield 53%).

$^1$H-NMR (400 MHz, CDCl$_3$): δ=8.47 (s, 1H), 8.12 (Is, 1H), 8.0 (d, 1H), 7.62 (d, 1H), 3.98 (s, 3H), 3.87 (s, 3H) ppm.

LC-MS RT 2.12, 504 (M+H$^+$), 545 (M+CH$_3$CN+H$^+$)

43

Example 11 (Step 13)

Preparation of 2-Chloro-5-[1-(2-methyl-5-pentafluoroethyl-4-trifluoromethyl-2H-pyrazol-3-yl)-1H-[L2,3]triazol-4-yl]-benzoic acid (see compound of formula (III''''))

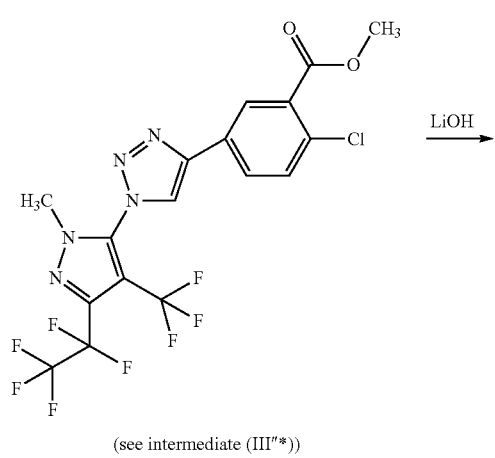

(see intermediate (III''*))

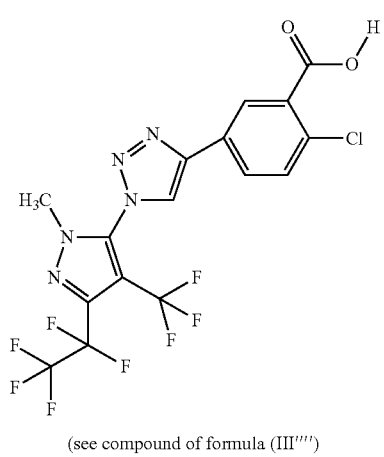

(see compound of formula (III''''))

2-Chloro-5-[1-(2-methyl-5-pentafluoroethyl-4-trifluoromethyl-2H-pyrazol-3-yl)-1H-[1,2,3]triazol-4-yl]-benzoic acid methyl ester (1.53 g, 3.0 mmol) is suspended in a mixture of water and tetrahydrofuran (1:3, 50 mL) and lithium hydroxide (0.22 g, 9.1 mmol) is added. The resulting mixture is stirred vigorously for 5 hours at 60° C. The reaction mixture is diluted with water and acidified with hydrogen chloride (2N). The aqueous phase is extracted twice with AcOEt, dried over MgSO$_4$ and concentrated under vacuum to afford the desired product 2-Chloro-5-[1-(2-methyl-5-pentafluoroethyl-4-trifluoromethyl-2H-pyrazol-3-yl)-1H-[1,2,3]triazol-4-yl]-benzoic acid. This compound was used without extra purification.

$^1$H-NMR (400 MHz, CDCl$_3$): δ=8.52 (s, 1H), 8.18 (Is, 1H), 8.09 (d, 1H), 7.66 (d, 1H), 3.88 (s, 3H) ppm.

LC-MS RT 2.08, 488 (M+H$^+$).

44

Example 12 (Step 8)

Preparation of N-[4-chloro-3-(benzylcarbamoyl)phenyl]-1-methyl-3-(pentafluoroethyl)-4-(trifluoromethyl)-1H-pyrazole-5-carboxamide (Compound (IIa))

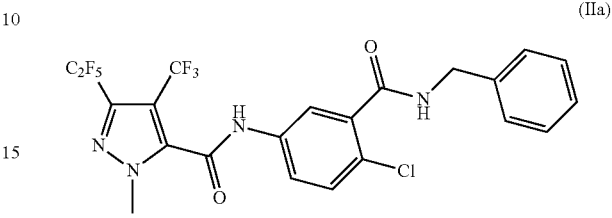

(IIa)

560 mg (1.79 mmol) of 1-methyl-3-pentafluoroethyl-4-trifluoromethylpyrazole-5-carboxylic acid were suspended in 10 ml of dichloromethane. The suspension was cooled to 0° C. and then subsequently admixed with 0.02 ml of N,N-dimethylformamide and 188 µl (2.15 mmol; 1.2 eq) oxalyl chloride. The reaction mixture was stirred firstly for 0.5 h at 0° C. and then for 3 hours at room temperature. The solvent was removed under reduced pressure on a rotary evaporator. The resulting 1-methyl-3-(pentafluoroethyl)-4-(trifluoromethyl)-1H-pyrazole-5-carbonyl chloride was used for the subsequent synthesis step without further work-up.

88.7 mg (0.34 mmol) of 5-amino-N-benzyl-2-chlorobenzamide, 2.77 mg (0.02 mmol) of N,N-dimethylpyridine-4-amine (DMPA) are dissolved in 2.5 ml of ethyl acetate. The solution is cooled to 0° C. using an ice bath and admixed with 119 µl (0.68 mmol) of N-ethyldiisopropylamine. 75.0 mg (0.22 mmol) of 1-methyl-3-(pentafluoroethyl)-4-(trifluoromethyl)-1H-pyrazole-5-carbonyl chloride are suspended in 2.5 ml of ethyl acetate and then added to the cooled reaction solution. The reaction mixture is heated for four hours at 50° C. and then stirred for 16 hours at room temperature. The reaction solution is diluted with 10.0 ml of ethyl acetate. The organic phase is washed three times with 1M hydrochloric acid, twice with 1M sodium hydroxide solution and once with saturated sodium chloride solution. The organic phase is dried over sodium sulphate and filtered and solvent is removed under reduced pressure on a rotary evaporator. This gives 140 mg (0.17 mmol) of N-[4-chloro-3-(benzylcarbamoyl)phenyl]-1-methyl-3-(pentafluoroethyl)-4-(trifluoromethyl)-1H-pyrazole-5-carboxamide (97%) as white solid.

$^1$H-NMR (400 MHz, d$_3$-acetonitrile): δ=9.29 (bs, 1H), 7.78 (d, 1H), 7.67 (dd, 1H), 7.48 (d, 1H), 7.21-7.52 (m, 6H), 4.54 (d, 2H), 3.97 (s, 3H) ppm.

HPLC-MS$^{a)}$: log P=3.90 mass (m/z)=555.1 [M+H]$^+$.

The invention claimed is:

1. Process for the synthesis of 5-fluoro-1H-pyrazole of formula (I)

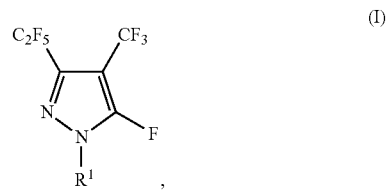

(I)

wherein R¹ represents $(C_1-C_4)$-alkyl;
comprising
reacting intermediate (3) with $(C_1-C_4)$-alkyl-CONHNH$_2$ to prepare 3-perfluoroethyl-4-perfluoromethyl-5-fluoro-pyrazol (intermediate (4))

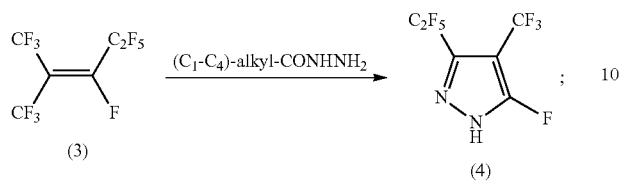

and
reacting intermediate (4) with an $(C_1-C_4)$-alkylation agent, optionally a methylation agent to prepare a compound of formula (I) (step 4).

2. Process for the synthesis of 5-fluoro-1H-pyrazole of formula (I) according to claim 1 comprising
Reacting hexafluoropropene (intermediate (1))

in the presence of a catalyst to form its dimer perfluoro-4-methyl-2-pentene (intermediate (2))

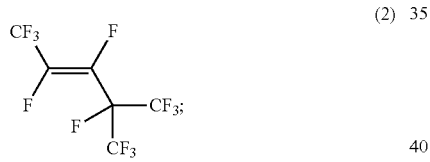

and
isomerizing perfluoro-4-methyl-2-pentene into perfluoro-2-methyl-2-pentene (intermediate (3))

and
reacting a compound (3) with $(C_1-C_4)$-alkyl-CONHNH$_2$ to prepare 3-perfluoroethyl-4-perfluoromethyl-5-fluoro-pyrazol (intermediate (4))

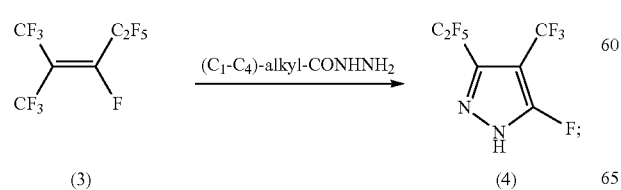

and
reacting intermediate (4) with an $(C_1-C_4)$-alkylation agent, optionally a methylation agent, to prepare a compound of formula (I).

3. Process for the preparation of a compound of formula (IV)

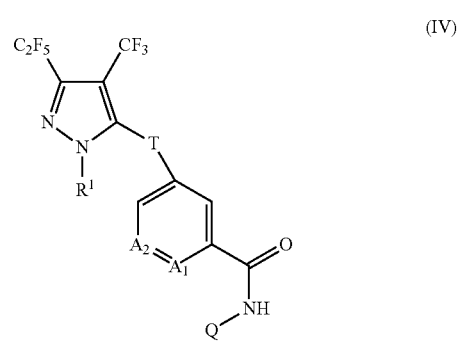

in which
R¹ is $C_1-C_4$-alkyl; and
A₁ is C—R²; and
R² is hydrogen, fluorine, chlorine, bromine, CN, NO₂, optionally halogenated $C_1-C_6$-alkyl, optionally halogenated $C_1-C_4$-alkoxy, optionally halogenated $C_1-C_4$-alkylsulphonyl, optionally halogenated $C_1-C_4$-alkylsulphinyl or N-cyclopropylaminocarbonyl (—C(═O)NH—cyclopropyl); preferably hydrogen, fluorine, chlorine, bromine, CN, NO₂, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, more preferably hydrogen, fluorine, chlorine, bromine, CN, NO₂, methyl, fluoromethyl, difluoromethyl, trifluoromethyl, 2,2,2-trifluoroethyl, methoxy, ethoxy, or pentafluoroethoxy, optionally hydrogen, fluorine, chlorine, bromine, most preferably chlorine; and
A₂ is C—R³ or nitrogen; and
R³ is hydrogen, methyl, fluorine or chlorine, optionally hydrogen; and
T represents one of the groups T1-T9 listed below, where the bond to the pyrazole head group is marked with an asterisk *,

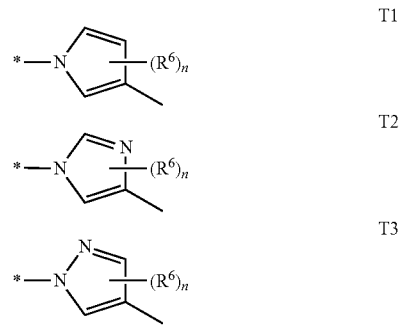

47
-continued

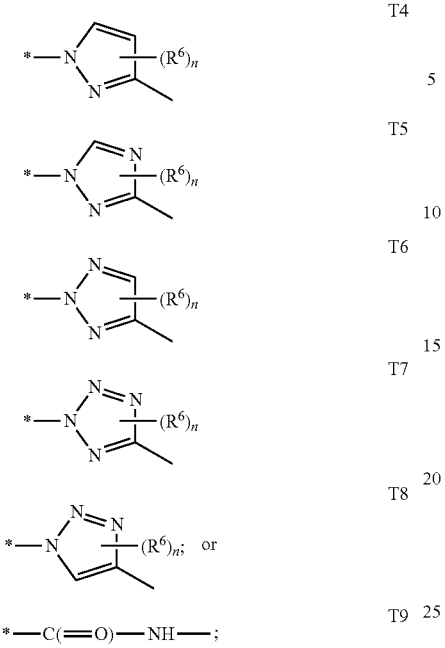

and

R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, optionally 0, provided that n is 0 or 1 in T5, T6 and T8 and provided n is 0 in T7; and Q is hydrogen, cyano, hydroxy, formyl or one of the groupings $C_1$-$C_6$-alkyl, $C_3$-$C_6$-alkenyl, $C_3$-$C_6$-alkynyl, $C_3$-$C_9$-cycloalkyl, $C_3$-$C_9$-heterocycloalkyl, $C_1$-$C_4$-alkoxy, $C_4$-$C_{15}$-alkylcycloalkyl, $C_4$-$C_{15}$-cycloalkylalkyl, $C_1$-$C_6$-hydroxyalkyl, $C_6$-aryl-$C_1$-$C_3$-alkyl, $C_5$-$C_6$-heteroaryl-$C_1$-$C_3$-alkyl, $C_1$-$C_4$-aminoalkyl, aminocarbonyl-$C_1$-$C_4$-alkyl or $C_1$-$C_4$-alkyl-amino-$C_1$-$C_4$-alkyl which are optionally substituted with one, two, three, four or five, optionally with one or two, optionally with one, substituents independently selected from the group consisting of hydroxy, nitro, amino, halogen, $C_1$-$C_3$-alkoxy, cyano, hydroxycarbonyl, $C_1$-$C_4$-alkoxycarbonyl, $C_1$-$C_4$-alkylcarbamoyl, $C_4$-$C_6$-cycloalkylcarbamoyl and optionally independently with one, two or three substituents selected from the group consisting of halogen, cyano, nitro, hydroxycarbonyl, $C_1$-$C_2$-alkylcarbamoyl, $C_1$-$C_2$-alkyl, halogenated $C_1$-$C_2$-alkyl and $C_1$-$C_2$-alkoxy substituted phenyl; preferably Q is $C_3$-$C_6$-cycloalkyl, or $C_3$-$C_6$-cycloalkyl which is substituted with at least one substituent selected from the group consisting of chlorine, fluorine, bromine, iodine, cyano and hydroxy, or $C_6$-aryl-$C_1$-$C_3$-alkyl; more preferably cyclopropyl, 1-cyano-cyclopropyl or benzyl (—CH₂—C₆H₅);

Comprising the process according to claim 1.

4. Process according to claim 3, wherein a compound of formula (IV) is a compound of formula (II)

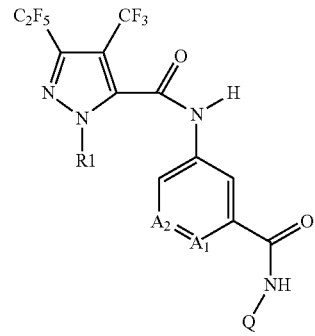

optionally of formula (II')

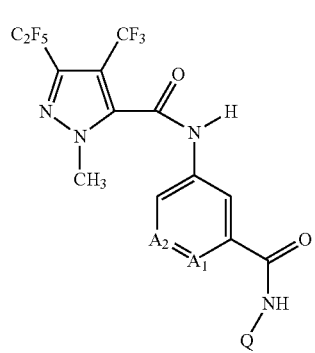

5. Process according to claim 3, wherein a compound of formula (IV) is compound (IIa)

(IIa)

6. Process according to claim 3, further comprising:
reacting compound (I) with a cyano-donor to prepare intermediate of formula (6)

(6)

wherein R¹ is (C₁-C₄)-alkyl; and reacting compound (6) with an inorganic strong base in a first hydrolysis step followed by adding an inorganic acid in a second hydrolysis step to prepare intermediate of formula (7)

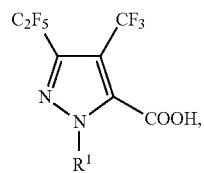

(7)

wherein
R¹ is (C₁-C₄)-alkyl; and
reacting a compound of formula (8) or its salt (8') with an activated form (7') of compound (7)

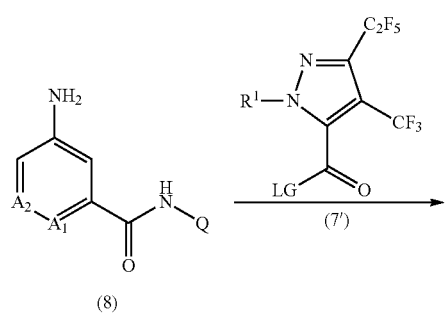

(II)

wherein R¹, A₁, A₂, and Q are as defined in claim 3 and LG is any leaving group, to prepare a compound of formula (II).

7. Process according to claim 3, wherein a compound of formula (IV) is a compound of formula (III)

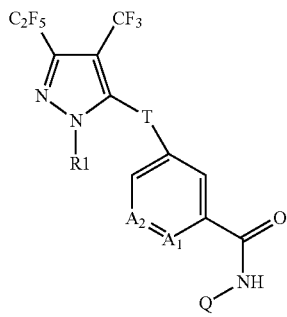

(III)

in which
R¹ is (C₁-C₄)-alkyl; and
A₁ is C—R²;
R² is hydrogen, fluorine, chlorine, bromine, CN, NO₂, optionally halogenated C₁-C₆-alkyl, optionally halogenated C₁-C₄-alkoxy, optionally halogenated C₁-C₄-alkylsulphonyl, optionally halogenated C₁-C₄-alkylsulphinyl or N-cyclopropylaminocarbonyl (—C(=O)—NH—cyclopropyl); optionally hydrogen, fluorine, chlorine, bromine, CN, NO₂, methyl, ethyl, fluoromethyl, difluoromethyl, trifluoromethyl, 2,2,2-trifluoroethyl, methoxy, ethoxy, n-propoxy, 1-methylethoxy, fluoromethoxy, difluoromethoxy, chlorodifluoromethoxy, dichlorofluoromethoxy, trifluoromethoxy, 2,2,2-trifluoroethoxy, 2-chloro-2,2-difluoroethoxy, pentafluoroethoxy, methylsulphonyl, methylsulphinyl, trifluoromethylsulphonyl, trifluoromethylsulphinyl or N-cyclopropylaminocarbonyl, optionally hydrogen, fluorine, chlorine, bromine, CN, NO₂, methyl, fluoromethyl, difluoromethyl, trifluoromethyl, 2,2,2-trifluoroethyl, methoxy, ethoxy, or pentafluoroethoxy, preferably hydrogen, fluorine, chlorine, bromine, most optionally chlorine; and
A₂ is C—R³ or nitrogen;
R³ is hydrogen, methyl, fluorine or chlorine, optionally hydrogen; and
Q is hydrogen, cyano, hydroxy, formyl or one of the groupings C₁-C₆-alkyl, C₃-C₆-alkenyl, C₃-C₆-alkynyl, C₃-C₉-cycloalkyl, C₃-C₉-heterocycloalkyl, C₁-C₄-alkoxy, C₄-C₁₅-alkylcycloalkyl, C₄-C₁₅-cycloalkylalkyl, C₁-C₆-hydroxyalkyl, C₆-aryl-C₁-C₃-alkyl, C₅-C₆-heteroaryl-C₁-C₃-alkyl, C₁-C₄-aminoalkyl, aminocarbonyl-C₁-C₄-alkyl or C₁-C₄-alkyl-amino-C₁-C₄-alkyl which are optionally substituted with one, two, three, four or five, optionally with one or two, optionally with one, substituents independently selected from the group consisting of hydroxy, nitro, amino, halogen, C₁-C₃-alkoxy, cyano, hydroxycarbonyl, C₁-C₄-alkoxycarbonyl, C₁-C₄-alkylcarbamoyl, C₄-C₆-cycloalkylcarbamoyl and optionally independently with one, two or three substituents selected from the group consisting of halogen, cyano, nitro, hydroxycarbonyl, C₁-C₂-alkylcarbamoyl, C₁-C₂-alkyl, halogenated C₁-C₂-alkyl and C₁-C₂-alkoxy substituted phenyl; optionally Q is C₃-C₆-cycloalkyl, or C₃-C₆-cycloalkyl which is substituted with at least one substituent selected from the group consisting of chlorine, fluorine, bromine, iodine, cyano and hydroxy, or C₆-aryl-C₁-C₃-alkyl; more preferably cyclopropyl, 1-cyano-cyclopropyl or benzyl (—CH₂—C₆H₅);

T represents one of the 5-membered heteroaromatics T1-T8 listed below, where the bond to the pyrazole head group is marked with an asterisk *,

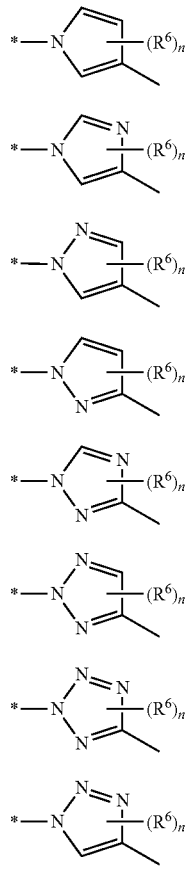

wherein
R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n represents the values 0-2, preferably 0, provided that n is 0 or 1 in T5, T6 and T8 and provided n is 0 in T7.

8. Process according to claim 7, wherein a compound of formula (III) is compound of formula (III'),

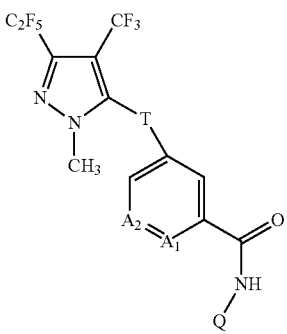

optionally compound (IIIa)

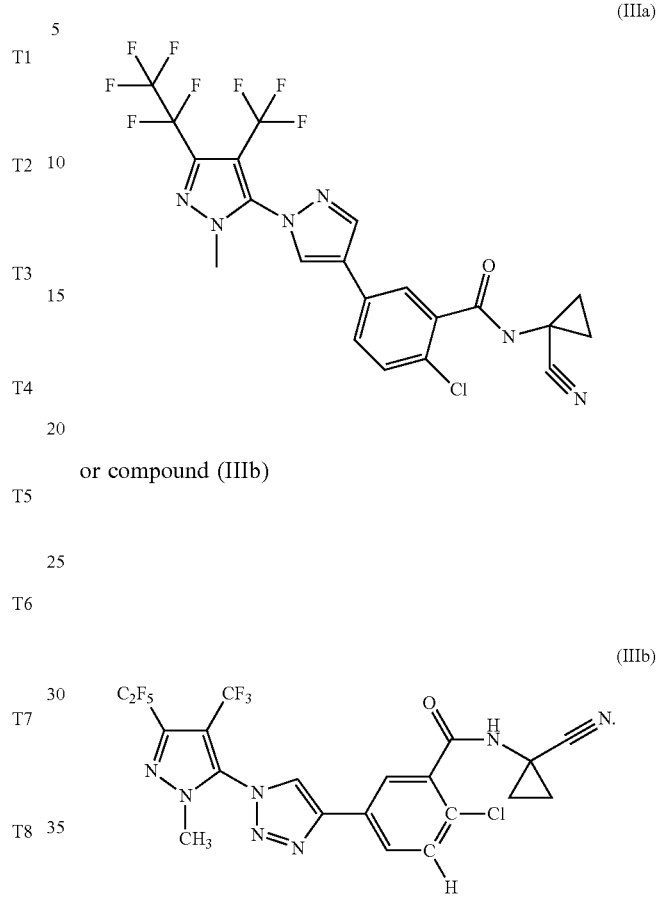

or compound (IIIb)

9. Process according to claim 7, comprising
reacting intermediate (3) with ($C_1$-$C_4$)-alkyl-CONHNH₂ to prepare 3-perfluoroethyl-4-perfluoromethyl-5-fluoro-pyrazol (intermediate (4))

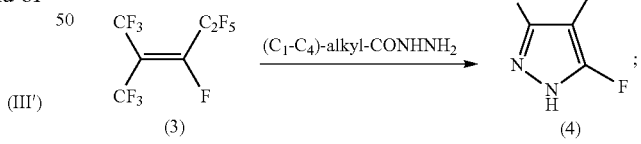

and
reacting intermediate (4) with an ($C_1$-$C_4$)-alkylation agent, optionally a methylation agent to prepare a compound of formula (I) (Step 4)
and further comprising
reacting a compound of formula (I) with an intermediate of formula (11) by nucleophilic substitution of the fluoride at the ring position of a compound of formula (I) (herein referred to as Step 9)

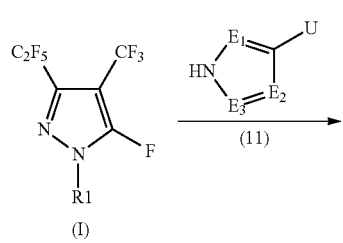

(I)

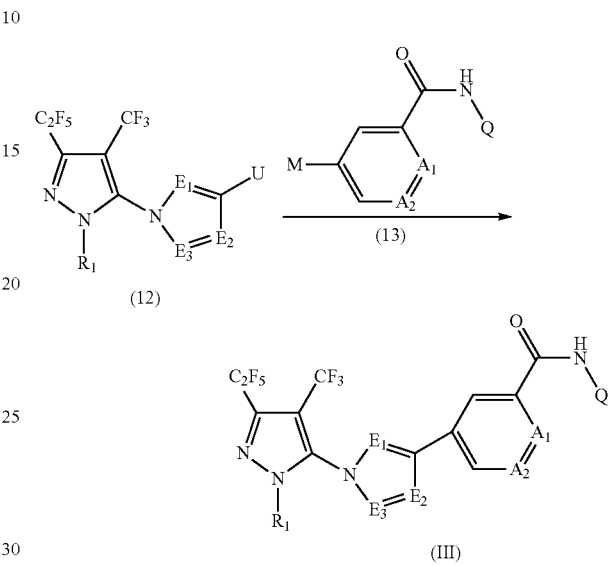

wherein
R¹ is optionally halogenated ($C_1$-$C_4$)-alkyl or optionally halogenated cyclopropyl; and
U represents bromine, iodine, triflate, boronic acid, boronic ester or trifluoroboronate; and
the five-membered cycles of $E_1$-$E_3$, carbon and nitrogen represent the 5-membered heterocycles selected from the group consisting of

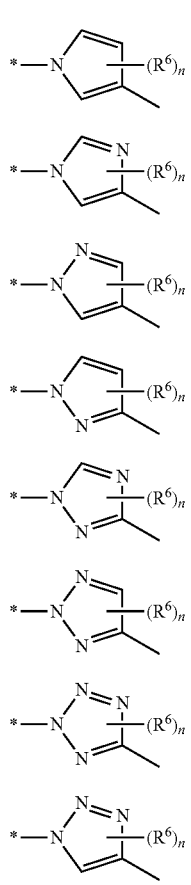

wherein
R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and
n represents the values 0-2, preferably 0, provided that n is 0 or 1 in T5, T6 and T8 and provided n is 0 in T7;
to prepare an intermediate of formula (12); and
reacting a compound of formula (12) and a compound of formula (13) (herein referred to as Step 10)

wherein R¹, $A_1$, $A_2$, and Q are as defined for a compound of formula (III) and
U represents bromine, iodine, triflate, boronic acid, boronic ester or trifluoroboronate; and
the five-membered cycles of $E_1$-$E_3$, carbon and nitrogen represent the 5-membered heterocycles selected from the group consisting of -continued

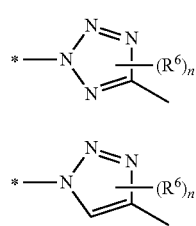
T7

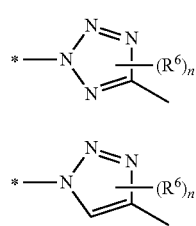
T8 wherein

R⁶ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, preferably 0, provided that n is 0 or 1 in T5, T6 and T8 and provided n is 0 in T7; and M represents bromine, iodine or triflate when U represents a boronic acid, boronic ester or trifluoroboronate; or M represents a boronic acid, boronic ester or trifluoroboronate when U represents bromine, iodine or triflate to prepare a compound of formula (III).

10. Process according to claim 3, wherein a compound of formula (IV) is a compound of formula (III″)

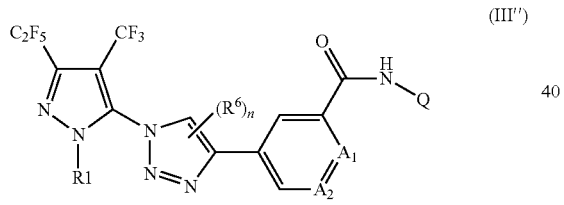
(III″)

optionally of formula (III‴)

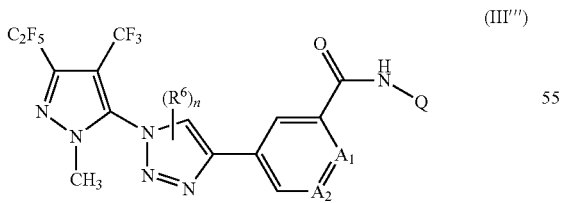
(III‴)

11. Process according to claim 10, comprising the process according to claim 1, either optionally further comprising reacting a compound of formula (I) with an intermediate of formula (11) by nucleophilic substitution of the fluoride at the ring position of a compound of formula (I) (herein referred to as Step 9)

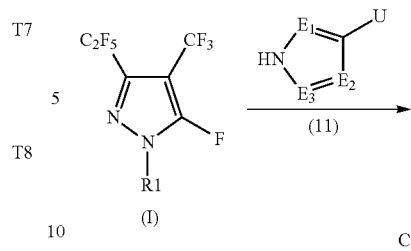

(I)

(11)

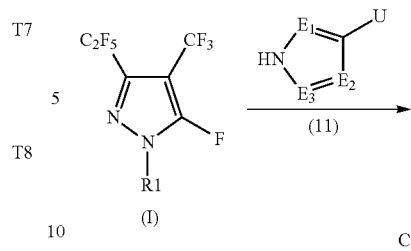

(12)

wherein

R¹ is optionally halogenated ($C_1$-$C_4$)-alkyl or optionally halogenated cyclopropyl; and U represents bromine, iodine, triflate, boronic acid, boronic ester or trifluoroboronate; and the five-membered cycles of $E_1$-$E_3$, carbon and nitrogen represent the 5-membered heterocycles selected from the group consisting of

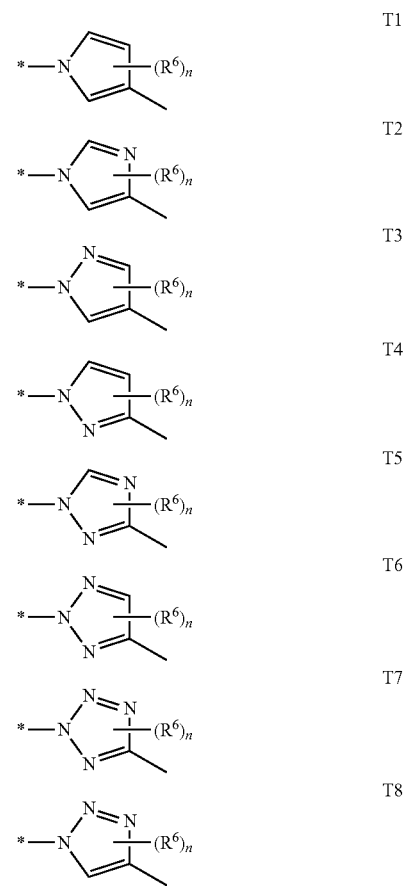

wherein

R⁶ independently of one another represents halogen, cyano, nitro, amino or optionally substituted $C_1$-$C_6$- alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, preferably 0, provided that n is 0 or 1 in T5, T6 and T8 and provided n is 0 in T7;

to prepare an intermediate of formula (12); and reacting a compound of formula (12) and a compound of formula (13) (herein referred to as Step 10)

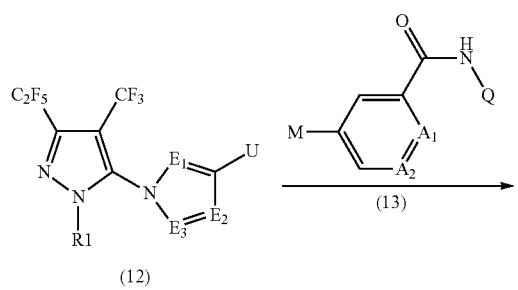

wherein $R^1$, $A_1$, $A_2$, and Q are as defined for a compound of formula (III) and U represents bromine, iodine, triflate, boronic acid, boronic ester or trifluoroboronate; and the five-membered cycles of $E_1$-$E_3$, carbon and nitrogen represent the 5-membered heterocycles selected from the group consisting of

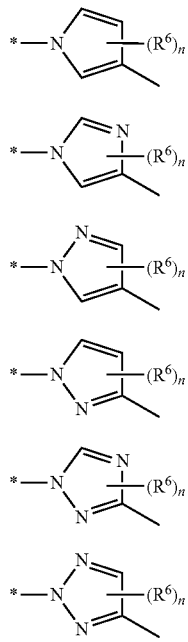

wherein $R^6$ independently of one another represents halogen, cyano, nitro, amino or optionally substituted $C_1$-$C_6$-alkyl, $C_1$-$C_6$-alkyloxy, $C_1$-$C_6$-alkylcarbonyl, $C_1$-$C_6$-alkylsulphanyl, $C_1$-$C_6$-alkylsulphinyl, $C_1$-$C_6$-alkylsulphonyl, and n represents the values 0-2, preferably 0, provided that n is 0 or 1 in T5, T6 and T8 and provided n is 0 in T7; and M represents bromine, iodine or triflate when U represents a boronic acid, boronic ester or trifluoroboronate; or M represents a boronic acid, boronic ester or trifluoroboronate when U represents bromine, iodine or triflate to prepare a compound of formula (III); or optionally further comprising reacting a compound of formula (I) and an azide-donoer to prepare intermediate (14)

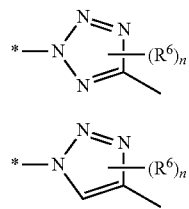

wherein $R^1$ is as defined for a compound of formula (III); and reacting intermediate (14) with an intermediate of formula (15) to give an intermediate (III"*) (Step 12)

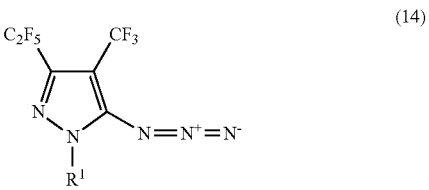

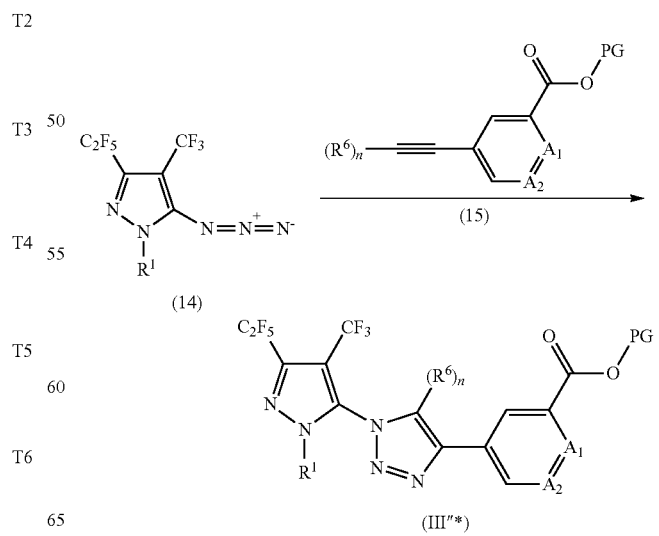

wherein $R^1$, $R^6$, $A_1$, and $A_2$ are as defined for compound (III), n is 0 or 1 and PG is any protective group of the carboxylic group such as $C_1$-$C_6$-alkyl (optionally, methyl).

12. Process according to claim 2, wherein $R^1$ is methyl.

13. Process according to claim 2, wherein step 3 and 4 are carried out in the same solvent, optionally acetonitrile or methylene chloride, optionally methylene chloride.

14. Process according to claim 2, wherein step 3 and 4 are carried out in the same solvent selected from the group consisting of acetonitrile or methylene chloride.

* * * * *